(12) United States Patent
Krusor et al.

(10) Patent No.: US 12,806,431 B2
(45) **Date of Patent: *Nov. 24, 2026**

(54) ELECTRONIC ELECTROCARDIOGRAM CALIPERS

(71) Applicant: Physio-Control, Inc., Redmond, WA (US)

(72) Inventors: Blaine Krusor, Seattle, WA (US); Ronald E. Stickney, Edmonds, WA (US); Michelle Liu, Redmond, WA (US); Christina Mason, Redmond, WA (US); Mike Chambers, Redmond, WA (US); Mark Rutzer, Seattle, WA (US); Jose Daniel Martinez Galan, Seattle, WA (US); Jason Fouts, Bothell, WA (US); Lisa Spencer, Redmond, WA (US)

(73) Assignee: Physio-Control, Inc., Redmond, WA (US)

( * ) Notice: Subject to any disclaimer, the term of this patent is extended or adjusted under 35 U.S.C. 154(b) by 252 days.

This patent is subject to a terminal disclaimer.

(21) Appl. No.: 18/818,425

(22) Filed: Aug. 28, 2024

(65) Prior Publication Data

US 2024/0419318 A1 Dec. 19, 2024

Related U.S. Application Data

(63) Continuation of application No. 18/485,763, filed on Oct. 12, 2023, now Pat. No. 12,105,947, which is a (Continued)

(51) Int. Cl.

*G06F 3/048* (2013.01)
*A61B 5/00* (2006.01)

(Continued)

(52) U.S. Cl.

CPC ............ *A61N 1/3993* (2013.01); *A61B 5/322* (2021.01); *A61B 5/339* (2021.01); *A61B 5/686* (2013.01);

(Continued)

(58) Field of Classification Search

CPC .. A61N 1/3993; A61N 1/3904; A61N 1/3925; A61N 1/37247; A61B 5/322;

(Continued)

(56) References Cited

U.S. PATENT DOCUMENTS

| | | |
|---|---|---|
| 4,989,610 A | 2/1991 | Patton et al. |
| 10,356,001 B1 | 7/2019 | Drakulic |

(Continued)

FOREIGN PATENT DOCUMENTS

| | | |
|---|---|---|
| EP | 2291851 A1 | 3/2011 |
| EP | 4276856 A1 | 11/2023 |

(Continued)

OTHER PUBLICATIONS

European Office Action mailed Nov. 17, 2022 for European Patent Application No. 20198390.5, a foreign counterpart to U.S. Appl. No. 17/033,380, 6 pages.

(Continued)

*Primary Examiner* — Aleksey Olshannikov
(74) *Attorney, Agent, or Firm* — Lee & Haves. P.C.

(57) ABSTRACT

Systems, devices, and methods relate to utilizing an electronic caliper to analyze an electronic electrocardiogram (ECG). An example method for includes outputting, by a display, an electronic ECG within a graphical user interface (GUI). An electronic caliper is output, by the display, as overlaid on the electronic ECG within the GUI. The electronic caliper includes a first electronic tip and a second electronic tip. The method further includes receiving, by a user input device, a user input signal and moving, based on (Continued)

the user input signal, the first electronic tip, the second electronic tip, or both the first electronic tip and the second electronic tip, relative to the electronic ECG within the GUI.

17 Claims, 18 Drawing Sheets

Related U.S. Application Data continuation of application No. 17/033,380, filed on Sep. 25, 2020, now Pat. No. 11,822,777.

(60) Provisional application No. 62/907,362, filed on Sep. 27, 2019.

(51) Int. Cl.

| | |
|---|---|
| ***A61B 5/322*** | (2021.01) |
| ***A61B 5/339*** | (2021.01) |
| ***A61N 1/39*** | (2006.01) |
| ***G06F 3/0485*** | (2022.01) |
| ***G06F 3/0488*** | (2022.01) |
| ***G06T 1/60*** | (2006.01) |
| ***G06T 11/60*** | (2006.01) |
| ***G16H 20/30*** | (2018.01) |
| ***G16H 40/67*** | (2018.01) |
| ***G16H 50/30*** | (2018.01) |
| *A61B 5/352* | (2021.01) |

(52) U.S. Cl.

CPC .......... *G06F 3/0485* (2013.01); *G06F 3/0488* (2013.01); *G06T 1/60* (2013.01); *G06T 11/60* (2013.01); *G16H 20/30* (2018.01); *G16H 40/67* (2018.01); *G16H 50/30* (2018.01); *A61B 5/352* (2021.01); *G06T 2200/24* (2013.01); *G06T 2210/41* (2013.01)

(58) Field of Classification Search

CPC ......... A61B 5/339; A61B 5/686; A61B 5/352; A61B 5/743; G06F 3/0485; G06F 3/0488; G06F 3/04883; G06T 1/60; G06T 11/60; G06T 2200/24; G06T 2210/41; G16H 20/30; G16H 40/67; G16H 50/30; G16H 40/63

See application file for complete search history.

(56) References Cited

U.S. PATENT DOCUMENTS

| | | | | |
|---|---|---|---|---|
| 2009/0054743 | A1 | 2/2009 | Stewart | |
| 2012/0075103 | A1* | 3/2012 | Powell ................. | A61B 5/0022 702/19 |
| 2012/0078665 | A1 | 3/2012 | Johnson et al. | |
| 2012/0278099 | A1 | 11/2012 | Kelly et al. | |
| 2013/0271469 | A1* | 10/2013 | Moore .................... | G06T 11/26 345/440.1 |
| 2014/0067279 | A1 | 3/2014 | George | |
| 2015/0199096 | A1 | 7/2015 | Kim et al. | |
| 2015/0282758 | A1 | 10/2015 | Chang | |
| 2017/0357764 | A1 | 12/2017 | Fauss et al. | |
| 2018/0250519 | A1 | 9/2018 | Chang | |
| 2019/0105504 | A1 | 4/2019 | Liu et al. | |
| 2019/0282112 | A1 | 9/2019 | Jia | |
| 2020/0357493 | A1* | 11/2020 | Kelly ..................... | G16H 10/60 |
| 2021/0096712 | A1 | 4/2021 | Krusor et al. | |
| 2024/0134514 | A1 | 4/2024 | Krusor et al. | |
| 2024/0231594 | A9 | 7/2024 | Krusor et al. | |

FOREIGN PATENT DOCUMENTS

| | | | |
|---|---|---|---|
| WO | WO2010066536 | A1 | 6/2010 |
| WO | WO2016134316 | A1 | 8/2016 |
| WO | WO2017204834 | A1 | 11/2017 |
| WO | WO2020169562 | A1 | 8/2020 |

OTHER PUBLICATIONS

Extended European Search Report mailed Feb. 9, 2021 for European Patent Application No. 20198390.5, 7 pages.

Office Action for U.S. Appl. No. 17/033,380, mailed on Jan. 17, 2023, Blaine Krusor, "Electronic Electrocardiogram Calipers", 17 pages.

Office Action for U.S. Appl. No. 17/033,380, mailed on May 11, 2022, Krusor, "Electronic Electrocardiogram Calipers", 15 pages.

Office Action for U.S. Appl. No. 17/033,380, mailed on Aug. 31, 2022, Krusor, "Electronic Electrocardiogram Calipers", 16 pages.

Search Report for European Patent Application No. 24151035.3, Dated Jun. 6, 2024, 7 pages.

* cited by examiner

ELECTRONIC ELECTROCARDIOGRAM CALIPERS

CROSS-REFERENCE TO RELATED APPLICATION

This application is a continuation of commonly assigned, U.S. patent application Ser. No. 18/485,763, filed Oct. 12, 2023, which is a continuation of U.S. patent application Ser. No. 17/033,380, filed Sep. 25, 2020, now granted U.S. Pat. No. 11,822,777, issued Nov. 21, 2023, which claims the benefit of U.S. Provisional Application No. 62/907,362, titled "Electronic ECG Calipers" and filed on Sep. 27, 2019. Application Ser. Nos. 18/485,793, 17/033,380 and 62/907,362 are fully incorporated herein by reference.

BACKGROUND

An electrocardiogram (ECG) is a plot of the electrical activity of a heart over time. The electrical activity of an individual is identified, for instance, by measuring relative voltages between various electrodes placed on the body of the individual. Care providers regularly analyze ECGs to identify, assess, and treat medical conditions in individuals. In various cases, the shape of features in an individual's ECG, the variance of features in the individual's ECG between different cardiac cycles, the duration of features in the individual's ECG, and the like, are indicative of whether the individual has an arrhythmia, or another particular type of medical condition. In some cases, care providers assess and/or recommend treatments for the medical condition based on the ECG.

Traditionally, ECGs are presented as physical printouts. For example, a printer prints one or more lines representing the ECG on a paper substrate. In some cases, the paper substrate is further printed with a grid that represents the scale of time and voltage with respect to the printed ECG. These printed ECGs are often analyzed by users (e.g., physicians, nurses, physician assistants, paramedics, or other medical care providers) using a physical caliper (also referred to as a "pair of calipers"). In general, a physical caliper is a device used to measure and/or identify a distance between two points in physical space. A physical caliper includes two tips. At least one of the tips is configured to move, such that the distance between the two tips is adjustable. When the tips are arranged at the two points, the distance between the tips corresponds to the distance between the two points. In some examples, the distance between the two tips is retained, even when the caliper is removed from the two points. Thus, the caliper can be used to efficiently measure the distance between the two points and/or compare the distance between the two points to another distance. In some examples, a user adjusts the tips of a caliper at two points in the printed ECG defining a first instance of a feature and moves the caliper to another two points defining a second instance of the feature in the printed ECG. The first and second instance, for example, correspond to respective cardiac cycles. Thus, the user assesses consistency, regularity, or irregularity within the ECG signal. In some cases, the user uses the physical caliper to measure the length (which may correspond to the duration) of a feature in the printed ECG. In various cases, the user assesses differences in the same type of segments of consecutive cardiac cycles, or between segments in a single cardiac cycle, to properly diagnose and treat the patient.

In various examples, the user moves the caliper in order to measure and/or compare features within the printed ECG.

However, as inherent with most human activity, there is a degree of error introduced when the caliper is moved. During the movement of the caliper, the interval between the tips could be lengthened or shortened due to inadvertent action by the user, such as a slight hand movement. Some circumstances of the environment, such as movement of patient transport (e.g., emergency vehicle) can inadvertently change the distance between the tips of the physical caliper.

With the trend towards paperless records, some medical devices (e.g., patient monitoring devices, patient treatment devices, and the like) display ECGs electronically. However, in various cases, physical calipers are unsuitable for electronic ECGs. For example, the tips of physical calipers can damage electronic displays outputting electronic ECGs. For instance, sharp caliper tips scratch electronic displays, break electronic displays, or the like. Additionally, physical calipers are prone to error when moved between different instances of features in electronic ECGs. Further, measuring distances, such as a distance representing a duration of a feature in an electronic ECG, is cumbersome and time-consuming.

There is a need in the art for improved ECG calipers that can be used with electronic displays, provide reductions of introduced error and provide more effective or efficient use of the ECG calipers when analyzing or assessing ECG signals.

DETAILED DESCRIPTION

Figure 1:
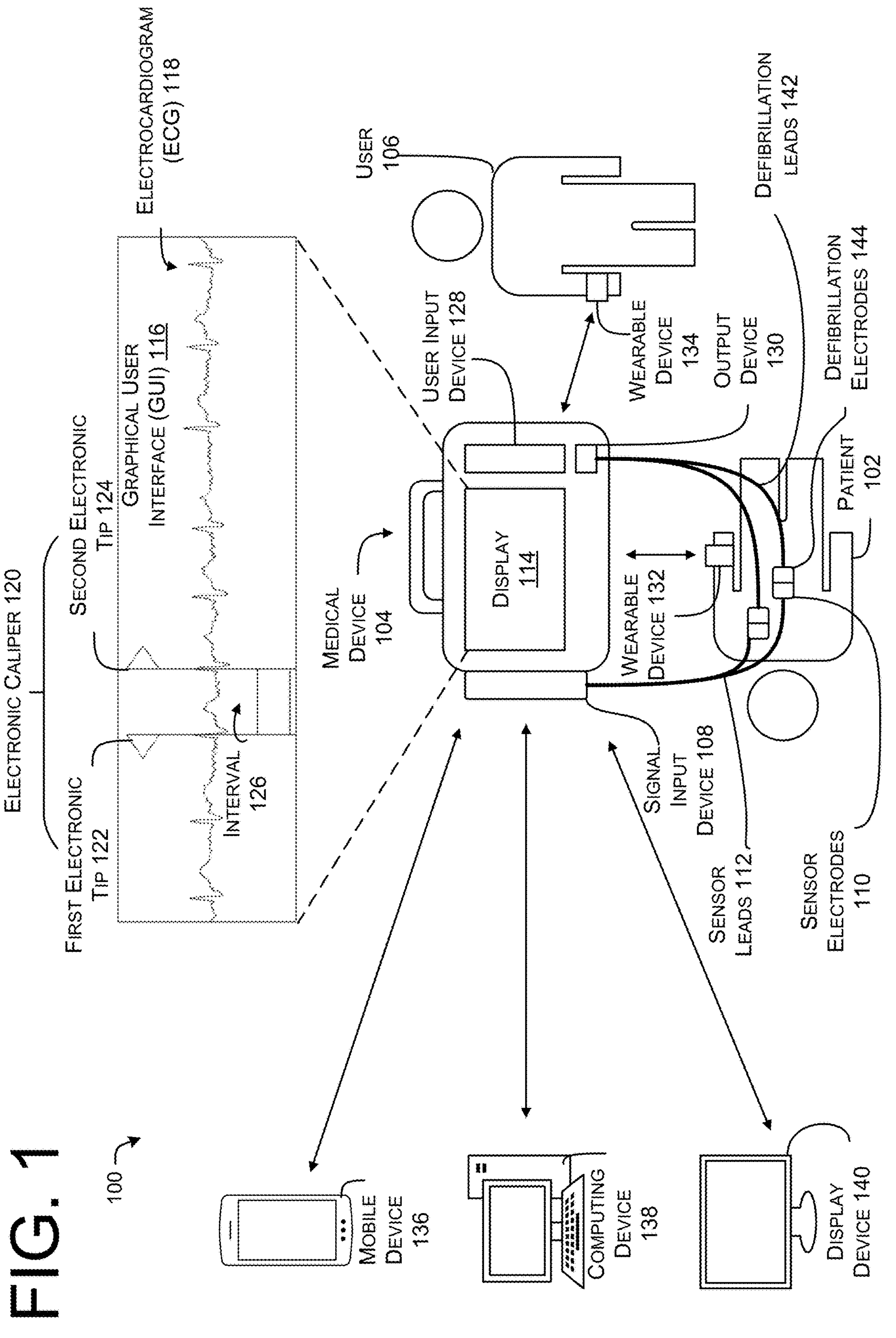
FIG. 1 illustrates an example environment for utilizing an electronic caliper for monitoring a condition of a patient.

Various implementations described herein relate to electronic calipers configured to facilitate analysis of electronic signals, such as ECGs, or other types of plots of physiological parameters over time. According to some examples, the physiological parameters exhibit periodicity. In various cases, an electronic ECG (also referred to as an "ECG signal" or a "digital ECG") of an individual is displayed as part of a graphical user interface (GUI) output by an electronic device. For example, the GUI is displayed on a display screen of the electronic device. The electronic ECG includes various features, whose duration and/or variation in the electronic ECG is clinically relevant to a medical condition of the individual. Examples of features include, for instance, a QRS complex, a PR interval (also referred to as a "PR segment"), a PR segment, an ST segment, a QT interval, or an RR interval of the electronic ECG. The electronic ECG, in some cases, further represents multiple instances of the features that are repeated in multiple cardiac cycles. For instance, the electronic ECG includes a first ST segment corresponding to a first heartbeat and a second ST segment corresponding to a second heartbeat. According to various examples described herein, the electronic device displays an electronic caliper overlaying the electronic ECG within the GUI. The electronic caliper includes one or more user interface elements that are output by the electronic device along with the electronic ECG.

According to some examples, the electronic caliper includes a first electronic tip (also referred to as a "first marker," a "first boundary," or a "first bound") and a second electronic tip (also referred to as a "second marker," a "second boundary," or a "second bound"). In various cases, the electronic device adjusts the positions of the first and second electronic tips, so that the tips overlay and/or intersect a particular feature of the electronic ECG. In some cases, the positions of the first and second electronic tips are adjusted based on at least one input signal (also referred to as a "user input") received by an input device from a user. According to some implementations, the input signal indicates a particular feature-of-interest within the electronic ECG and the electronic device automatically locates the first and second electronic tips at the specified feature. For example, the user selects a feature of the electronic ECG using an input mechanism (e.g., touchscreen, button, track pad, or the like). In some cases, the user selects the feature from a list (e.g., a drop-down menu in the GUI) of predetermined ECG signal features. The electronic ECG is analyzed to identify the selected feature within the electronic ECG. The electronic caliper is positioned at the identified feature so that the first electronic tip of the caliper is aligned with a beginning of the feature, and the second electronic tip of the caliper is aligned with an end of the feature. In some examples in which the feature is a PR interval, the first electronic tip of the electronic caliper is aligned with the beginning of the PR interval, and the second electronic tip of the electronic caliper is aligned with the end of the PR interval. For instance, the first electronic tip overlays a beginning of the P wave within the displayed electronic ECG and the second electronic tip may overlay the beginning of a QRS complex within the displayed electronic ECG. In some cases, the input signal from the user indicates a direction and/or a position within the GUI and the electronic device moves one or both of the first and second electronic tips based on the direction and/or position. Thus, the position of the electronic caliper is adjustable by a user.

When multiple instances of a selected feature are present in the electronic ECG, in some cases, the user selects a particular instance of the feature on which at least a portion of the electronic caliper will be overlaid. In some cases, the electronic caliper is automatically displayed on a default instance of the feature. For example, the electronic caliper is overlaid on the first (e.g., earliest) instance of the feature within the electronic ECG output in the GUI. In some cases, a default position of the electronic caliper, upon activation, is a center of the displayed electronic ECG, a left side of the displayed electronic ECG, or the like. In some examples in which the feature is an RR interval and the displayed ECG signal includes multiple RR intervals, the electronic caliper is displayed on the first (e.g., the earliest) RR interval within the displayed electronic ECG. That is, the electronic caliper is displayed between two cardiac cycles in the ECG signal, wherein the first tip of the caliper overlays the R wave in the first cardiac cycle and the second tip of the caliper overlays the R wave in the second cardiac cycle.

In various examples, a separation between the first and second electronic tips corresponds to a time interval in the electronic ECG. A caliper interval (also referred to as an "interval") is defined between the first electronic tip and the second electronic tip. As used herein, the caliper interval includes a distance and/or a space that extends between the first tip and the second tip of the electronic caliper. The electronic device is configured to identify the time period corresponding to the caliper interval and output an indication of the time period to the user, in some cases. For example, if the first electronic tip is located at a first position on the electronic ECG corresponding to the end of an S wave, and the second electronic tip is located at a second position on the electronic ECG corresponding to the beginning of a T wave, then the electronic device is configured to output an accurate duration of the corresponding ST segment. In some cases, the electronic device identifies the time period indicated between the electronic tips of the electronic caliper, whose positions relative to the electronic ECG may have been positioned by a user. The duration is output in units of time, such as milliseconds, for example.

In some cases, the electronic caliper is moved while retaining a relative distance between the first and second electronic tips. In some cases, the electronic caliper is moved relative to the electronic ECG. For example, the electronic caliper is repositioned while maintaining the caliper interval, such that the same time interval is indicated by the electronic caliper even when the first electronic tip and the second electronic tip are repositioned. In various examples, the displayed ECG is moved relative to the electronic caliper, such as to display preceding, or proceeding, portions of the electronic ECG that were not previously displayed. In various examples described herein, moving the electronic ECG within the GUI (e.g., relative to the electronic caliper) can be referred to as "scrolling" the electronic ECG.

According to some implementations, the electronic caliper is repositioned based on an input signal received by an input device from a user. In some examples, the electronic device outputs the electronic caliper to be overlaid on and/or intersecting a first instance of a particular feature and then repositions the electronic caliper to at least partially overlay and/or intersect a second instance of the particular feature. For example, if the first and second electronic tips of the electronic caliper are initially located on a PR interval of a first cardiac cycle in the electronic ECG, the electronic caliper is moved to a PR interval of a second cardiac cycle in the electronic ECG, such that the first electronic tip overlays the beginning of the P wave in the second cardiac cycle. Moving the electronic caliper between different instances of the same feature in the electronic ECG enables a user to efficiently identify how the feature varies over time. For example, after the electronic caliper is repositioned to the PR interval of the second cardiac cycle, the user is able to identify whether the PR interval of the second cardiac cycle is longer or shorter than the PR interval of the first cardiac cycle by comparing the location of the second tip to the beginning of the R wave of the second cardiac cycle in the electronic ECG. Moving the electronic caliper within the GUI facilitates patient diagnosis.

In some examples, the user moves the electronic caliper between instances of a particular feature in the electronic ECG. In some cases, the electronic caliper is moved from an initial instance of the feature to another instance of the feature while maintaining the caliper interval associated with the initial instance of the feature. In some cases, the electronic caliper is moved from an initial instance of the feature to another instance of the feature while adjusting to the caliper interval of the other instance of the feature. For example, the electronic caliper is displayed on an initial instance of a PR interval in electronic ECG, then moved to a different instance of the PR interval in the electronic ECG, which may show whether the second instance of the PR interval is different from the first instance of the PR interval. Variations of a feature in different cardiac cycles of an ECG are indicative of medical conditions. For example, a difference between the first and second instances of the PR interval correlates with second degree atrioventricular block, Mobitz type 1. The use of the electronic caliper can assist users with analyzing or assessing the electronic ECG, thereby enabling users and/or medical devices to accurately and efficiently diagnose a patient with a medical condition. Examples of the medical condition include atrial fibrillation (AF), ventricular fibrillation (VF), ventricular tachycardia (VT or V-Tach), atrioventricular (AV) block (e.g., first degree; second degree, such as Mobitz type 1 or type 2; third degree), long QT interval, ST-elevation myocardial infarction (STEMI), or the like.

According to some examples, the electronic caliper is duplicated while retaining the relative distance between the first and second tips. In various implementations described herein, duplicating the electronic caliper can be referred to as "marching" the electronic caliper. In some cases, the electronic caliper is selectively repeated along the electronic ECG. For instance, the repeated electronic calipers are repeated consecutively along the electronic ECG, with the first electronic tip of one of the duplicated calipers aligned with the second electronic tip of another one of the duplicated calipers. For example, one or more duplications of the electronic caliper, each with pairs of electronic tips that are respectively separated by the same relative distance, are output on the electronic ECG. In some cases, the duplications of the electronic caliper overlap, such that one tip of a first duplication overlaps or is equivalent to a tip of a second duplication. In particular examples, the duplicated calipers are displayed exclusively to the right of the original electronic caliper. In some cases, the electronic device outputs the duplications on respective instances of a particular feature in the electronic ECG. In an illustrative example, the electronic caliper is output on a first instance of a PR segment such that the relative distance between the first and second tip corresponds to the duration of the first instance of the PR segment. Duplications of the electronic caliper are output on other instances of the PR segment in the electronic ECG, such that the first electronic tip of each duplication overlaps the end of the P wave of each PR segment. In some cases, the second electronic tip of each duplication is located at a location that retains the relative distance between the first and second electronic tips of the initial electronic caliper. Thus, by viewing the duplicated electronic caliper, the user can efficiently identify changes in the feature over multiple cardiac cycles. Duplicating the electronic caliper facilitates patient diagnosis.

In various cases, the electronic device outputs the electronic ECG with other elements that facilitate ECG analysis. In some examples, the electronic ECG is output with a grid. In some cases, the grid corresponds to one or more of the electronic tips of the electronic caliper, such that a gridline of the grid is aligned with one of the electronic tips of the electronic caliper. Each box in the grid has a height corresponding to the voltage scale of the electronic ECG and a width corresponding to the time scale of the electronic ECG. Thus, the user can efficiently estimate the magnitude and/or duration of various portions of the ECG.

According to some implementations, the view of the electronic ECG output on the GUI is adjusted. In some examples, the view is adjusted based on an input signal received by an input device from a user. In some cases, the electronic device is configured to zoom in or zoom out on the electronic ECG, thereby adjusting the relative size of features of the electronic ECG as output to the user. According to some examples, the electronic device is configured to change the scale (e.g., the voltage scale and/or the time scale) of the electronic ECG. In some implementations, the electronic device changes the segment of the electronic ECG that is output on the GUI. For example, the electronic device may initial display the first minute of the electronic ECG, and then may adjust the GUI to display the third minute of the electronic ECG, or the like.

Various devices, systems, and methods utilizing electronic calipers provide improvements to conventional, physical calipers. Various implementations of the electronic calipers improve the effectiveness and efficiency of patient diagnosis based on electronic ECGs. For example, an electronic caliper accurately identifies and/or measures features in an electronic ECG without damaging a screen outputting the electronic ECG. Unlike physical calipers, the described electronic calipers maintain a fixed interval free of inadvertent adjustment due to movement. Additionally, unlike physical calipers, the electronic caliper efficiently adapts to changes in the display of the electronic ECG, such as changes to the time scale of the displayed electronic ECG that might occur when zooming in or out on the electronic ECG. In various cases, the features of an electronic ECG are measured more accurately using implementations of the electronic caliper than using a physical caliper. These and other advantages provide a practical application to the technical field of computer-based medical diagnostics.

Described herein are systems and methods of electronic calipers that include their display, use, and manipulation. An ECG signal can be received by an entity including a computing system, a computing device, medical device, or the like. The entity displays the ECG signal. The entity selectively displays an electronic caliper overlaid on the displayed the ECG signal.

Although various implementations described herein relate to displaying an electronic caliper on an electronic ECG, the scope of this disclosure is not so limited. In various examples, the electronic caliper is displayed, overlaid, repositioned, duplicated, or otherwise manipulated, on a graphical display of an impedance of an individual over time, an oxygenation (e.g., $SpO_2$) of an individual over time, a partial pressure of $CO_2$ (e.g., $EtCO_2$) in respiration of an individual over time, a pulse of an individual over time, or the like. According to some implementations, the electronic caliper enhances measurements and/or analysis of periodic features in a plot of a physiological parameter of an individual over time.

FIG. 1 illustrates an example environment 100 for utilizing an electronic caliper for monitoring a condition of a patient 102. As illustrated, the environment 100 includes the patient 102, who is monitored by a medical device 104. According to some implementations, the medical device 104 is a defibrillator. For example, the medical device 104 is an external defibrillator, such as an automated external defibrillator (AED) or a monitor-defibrillator. In some cases, the medical device 104 is a portable medical device. A user 106 may utilize the medical device 104 to evaluate a condition of the patient 102. Although illustrated in FIG. 1 as separate individuals, in some cases, the patient 102 is the user 106.

The medical device 104 includes a signal input device 108 that detects physiological parameters of the patient 102. In some cases, the physiological parameters indicate a condition of a heart of the patient 102. According to various examples, the physiological parameters include a voltage generated by the heart of the patient 102, an electrical impedance of the patient 102, a heart rate of the patient 102, a pulse oximetry level of the patient 102, or any combination thereof. In some examples, the signal input device 108 includes one or more ports configured to receive analog signals indicative of the physiological parameters. The one or more ports may be electrically coupled to one or more sensors.

According to various examples, the physiological parameters detected by the signal input device 108 include an electrical signal output by the heart of the patient 102. Sensor electrodes 110 are coupled to the patient 102. For instance, the sensor electrodes 110 are adhered to the patient 102 via an adhesive. The sensor electrodes 110 receive an electrical signal (e.g., the voltage) output by the heart of the patient 102. Sensor leads 112 electrically couple the sensor electrodes 110 to the signal input device 108. In some cases, the signal input device 108 is configured to convert the electrical signal into digital data indicative of an ECG 118 (also referred to as an "ECG signal 118") of the patient 102. Although FIG. 1 illustrates a pair of sensor electrodes 110, in some examples, the signal input device 108 receives electrical signals indicative of the ECG 118 from three or more sensor electrodes 110. For example, a 12-lead ECG is obtained from ten sensor electrodes 110 placed on the skin of the patient 102. In some cases, the signal input device 108 includes an analog to digital converter.

The medical device 104 includes a display 114 configured to graphically output the physiological parameters. As shown in the example of FIG. 1, the display 114 outputs a graphical user interface (GUI) 116 that includes at least a portion of the ECG 118 of the patient 102. The ECG 118 includes a first axis corresponding to time and a second axis corresponding to voltage. As illustrated in FIG. 1, the horizontal axis of the ECG 118 represents time and the vertical axis of the ECG 118 represents voltage. In some cases, the GUI 116 includes multiple plots corresponding to different (e.g., 12) leads of the ECG 118.

In various examples, the user 106 views the GUI 116 output by the display 114 and evaluates the ECG 118 of the patient 102 based on the GUI 116. Various medical conditions of the patient 102 are associated with changes in the ECG 118 of the patient 102 over time. To facilitate evaluation by the user 106 of a medical condition of the patient 102, the medical device 104 outputs an electronic caliper 120 (also referred to as a "displayed caliper," a "virtual caliper," or a "electronic ECG caliper") within the GUI 116.

As illustrated, the electronic caliper 120 includes a first electronic tip 122 (also referred to as a "first marker," a "first boundary," or a "first bound") and a second electronic tip 124 (also referred to as a "second marker," a "second boundary," or a "second bound"). The first electronic tip 122 and the second electronic tip 124 are GUI elements overlaid and/or intersecting on the ECG 118 within the GUI 116. For instance, the first electronic tip 122 and the second electronic tip 124 each include a vertical line that intersects the ECG 118. In some cases, the first electronic tip 122 and the second electronic tip 124 each include a flag, which is a user interface element having a particular shape (e.g., a triangular shape, a circular shape, a shape with one flat side and one curved side, or some other type of shape), that enhances the visibility of the electronic tip 122 or 124. The first electronic tip 122 is overlaid on and/or intersecting a first portion (e.g., a first point) of the ECG 118 associated with a first time. The second electronic tip 124 is overlaid on and/or intersecting a second portion (e.g., a second point) of the ECG 118 associated with a second time, wherein the first time is earlier than the second time. The first electronic tip 122 is spaced apart from the second electronic tip 124 by an interval 126. A length of the interval 126 corresponds to a time difference between the first time and the second time. For instance, as illustrated in FIG. 1, the first electronic tip 122 and the second electronic tip 124 are spaced apart along the horizontal time axis by an interval 126 (also referred to as a "caliper interval"), such that the horizontal distance between the first bound 122 and the second bound 124 corresponds to a time interval within the ECG data of the plot 118. In some cases, the interval 126 is a space between the first electronic tip 122 and the second electronic tip 124. In some examples, a spacer, such as a rectangular bar and/or line, spans the interval 126 and extends between the first electronic tip 122 and the second electronic tip 124.

In some cases, the medical device 104 outputs the caliper 120 based on an input signal received from the user 106. The medical device 104 includes a user input device 128 configured to receive inputs from the user 106. In some examples, the user input device 128 includes a keypad, a cursor control, a touch-sensitive display (also referred to as a "touchscreen"), a voice input device, a haptic feedback device, a button, a track pads, a keyboard, or any combination thereof. In some cases, the user input device 128 includes touch sensors integrated with the display 114, such that the user input device 128 senses the touch of the user 106 on the display 114. For instance, the display 114 is a touchscreen including one or more touch sensors configured to receive the input signal from the user 106. The touch can be received, by the medical device 104, as an input signal (also referred to as a "user input") from the user 106.

According to various implementations, an input signal from the user 106 indicates and/or selects a feature of the ECG 118. The medical device 104 generates and/or outputs the electronic caliper 120 within the GUI 116 based on the selected feature. For example, the medical device 104 outputs a list indicating a variety of features of the ECG 118. In various instances, the features include a PR interval, a PQ segment, a QRS complex, an ST segment, a QT interval, an RR interval, or any combination thereof. In some cases, the list is displayed graphically within the GUI 116. For example, the list is output as a drop-down menu within the GUI 116. In some examples, the user input device 128 receives an input signal from the user 106 selecting one of the features. In response, the medical device 104 identifies at least one instance of the selected feature within the ECG 118. As used herein, the terms, "instance," "feature instance," and their equivalents can refer to a single example of a repeated feature. For example, the ECG 118 represents the electrical signal of the heart of the patient 102 over the course of multiple cardiac cycles, with various features (e.g., a PR interval, a PQ segment, a QRS complex, an ST segment, a QT interval, or the like) that repeat in multiple cardiac cycle. The medical device 104 outputs the electronic caliper 120 in a position within the GUI 116 that corresponds to at least one instance of the identified feature. For example, the first electronic tip 122 is output overlaying and/or intersecting a beginning of an instance of the feature and the second electronic tip 124 is output overlaying and/or intersecting an end of the instance of the feature.

In particular examples, the user 106 selects, from a drop-down menu output on the GUI 116, an RR interval feature of the ECG 118. In response to the selection by the user 106, the medical device 104 identifies the RR interval of the ECG 118 by analyzing the data indicative of the ECG 118. For example, the medical device 104 identifies an instance of the RR interval in the ECG 118 by identifying voltage peaks in adjacent cardiac cycles of the ECG 118, wherein the voltage peaks represent the peaks of the R waves of the adjacent cardiac cycles. The medical device 104 outputs the first electronic tip 122 intersecting a first R peak of the ECG 118 and outputs the second electronic tip 124 intersecting a second R peak of the ECG 118. The interval 126 of the electronic caliper 120 corresponds to the RR interval between the first R peak and the second R peak.

According to some implementations, a position of the electronic caliper 120 is manually adjustable. For example, the medical device 104 receives a signal, from the user 106, indicating a movement of the first electronic tip 122, the second electronic tip 124, or a combination thereof. The medical device 104, in response, moves the first electronic tip 122 and/or the second electronic tip 124 in accordance with the signal from the user 106. In some cases, the medical device 104 moves the electronic caliper 120 in accordance with the signal from the user 106, wherein the interval 126 between the first electronic tip 122 and the second electronic tip 124 is retained after the electronic caliper 120 is moved.

In some cases, the medical device 104 duplicates the electronic caliper 120. For example, the medical device 104 outputs at least one duplicated caliper overlaying the ECG 118, wherein each duplicated caliper includes a pair of electronic tips that are separated by intervals with the same length as the interval 126. In some cases, each duplicated caliper includes an electronic tip that overlaps and/or intersects with a beginning of an instance of the selected feature or an end of the instance of the selected feature. According to some implementations, an electronic tip of a duplicated caliper overlaps or is equivalent to the first electronic tip 122 or the second electronic tip 124. In some cases, the duplicated calipers enable the user 106 to efficiently view variations between different instances of a feature in the ECG 118.

In various examples, the medical device 104 is configured to output an indication of the interval 126. For example, the medical device 104 identifies a time period corresponding to the interval 126 and outputs an indication of the time period to the user. In various implementations, the interval 126 is adjusted by the user 106, the medical device 104 determines the time period corresponding to the adjusted interval 126, and/or outputs the indication of the time period. In various cases the time period corresponding to the interval 126 is a duration of the selected feature. If the selected feature is an RR interval, for example, then the medical device 104 outputs the duration of the RR interval. In various examples, the medical device 104 outputs the indication of the interval 126 on the display 114. In some cases, the medical device 104 outputs the indication of the interval 126 via an output device 130. The output device 130 includes, for example, a speaker configured to output audio indicative of the interval 126, a printer configured to print a substrate with an indication of the interval 126, or the like. Thus, the indication of the interval 126 is output, in various implementations, as a visual signal, an auditory signal, a haptic signal (e.g., as vibration), or the like.

The medical device 104 is configured to output additional elements within the GUI 116. For example, the medical device 104 selectively outputs a grid within the GUI 116. The ECG 118 overlays the grid, in some cases. The grid includes squares, each with a width corresponding to a particular time interval and a height corresponding to a particular voltage. For example, the width of each square corresponds to 0.04 seconds, 0.2 seconds, or the like. In some cases, the height of each square corresponds to 0.1 mV, 0.5 mV, or the like. The grid is indicative of a time and/or voltage scale of the ECG 118 and can therefore help the user 102 visually estimate times and/or voltages associated with the ECG 118. In some examples, a line of the grid (e.g., a vertical line of the grid) is output underlaying one of the first electronic tip 122 or the second electronic tip 124.

The medical device 104 is configured to manipulate the GUI 116 in a variety of ways. In some examples, the medical device 104 presents the information displayed by the GUI 116 based on an input signal form the user 106. According to some examples, the medical device 104 zooms in or zooms out the ECG 118 within the GUI 116. In some cases, the medical device scrolls through the ECG 118 within the GUI. Thus, the medical device 104 is configured to change how much and/or what portion of the ECG 118 is displayed within the GUI 116. For example, the GUI 116 initially displays a particular portion of the ECG 118 and is adjusted to display a portion of the ECG 118 that proceeds the particular portion (also referred to as a "proceeding portion") and/or a portion of the ECG 118 that precedes the particular portion (also referred to as a "preceding portion").

In various implementations of the present disclosure, the medical device 104 is configured to communicate with external devices. For example, the medical device 104 is configured to transmit and/or receive data with a wearable device 132 of the patient 102, a wearable device 134 of the user 106, a mobile device 136, a computing device 138, a display device 140, or any other type of electronic device configured to transmit and/or receive the data. The data is transmitted over one or more wireless communication links (e.g., a WI-FI® link, a WIGIG® link, a BLUETOOTH® link, a radio link, a near field communication (NFC) link, or the like), one or more wired communication links (e.g., an Ethernet link, an optical fiber link, or the like), or a combination thereof. In some cases, the data is transmitted over one or more communication networks, such as a local area network (LAN), a wide area network (WAN) (e.g., the Internet), a mobile core network (e.g., a 3$^{rd}$ Generation Partnership Project (3GPP) network), a radio access network (RAN), or any combination thereof. According to various examples, any of the wearable device 132 of the patient 102, the wearable device 134 of the user 106, the mobile device 136, the computing device 138, and the display device 140 includes a display configured to output the GUI 116 in any manner equivalent to the display 114 of the medical device 104. For example, the medical device 104 transmits data indicative of the GUI 116, the ECG 118, the electronic caliper 120, or a combination thereof, to an external device (e.g., the wearable device 132 of the patient 102, the wearable device 134 of the user 106, the mobile device 136, the computing device 138, or the display device 140), thereby causing the external device to output any portion of the GUI 116 on its respective display. In some examples, any of the wearable device 132 of the patient 102, the wearable device 134 of the user 106, the mobile device 136, the computing device 138, and the display device 140 includes an input device configured to receive an input signal from the user 106 in any manner equivalent to the user input device 128 of the medical device 104. For example, the medical device 104 receives data indicative of the user input signal from an external device (e.g., the wearable device 132 of the patient 102, the wearable device 134 of the user 106, the mobile device 136, the computing device 138, or the display device 140), thereby enabling the user 106 to input signals to the medical device 104 via the external device.

The wearable device 132 of the patient 102 and the wearable device 134 of the user 106 are configured to receive and/or transmit data wirelessly with the medical device 104. In some examples, the wearable device 132 and/or the wearable device 134 includes a smartwatch, smart clothing, smart glasses, or any combination thereof. In various examples, the wearable device 132 is configured to be worn by the patient 102 and the wearable device 134 is configured to be worn by the user 106.

According to various implementations, the mobile device 136 is a user equipment (UE) configured to receive and/or transmit data wirelessly with the medical device 104. In some cases, the mobile device 136 includes a cellphone (e.g., a smartphone), a personal digital assistant (PDA), a tablet computer, or the like. In various examples, the mobile device 146 includes an internet of things (IoT) device.

In various examples, the computing device 138 includes any computing system configured to receive and/or transmit data with the medical device 104. In some cases, the computing device 138 communicates over one or more wired and/or wireless communication links. The computing device 138 includes, for example, a desktop computer, a laptop computer, a server computer, or any combination thereof.

The display device 140, for example, includes an external device configured to display the GUI 116 and/or other information output by the medical device 104. For example, the display device 140 includes a television (e.g., a smart TV), a monitor, a projector, or the like.

In various implementations, the medical device 104 is a defibrillator configured to output a defibrillation shock and/or a pacing signal to the patient 102. The output device 130 is connected to a set of defibrillation leads 142. The defibrillation leads 132 are connected to defibrillation electrodes 144 that are in contact with the skin of the patient 102. According to some examples, the defibrillation electrodes 144 are integrated with, or at least partially in contact with, at least some of the sensor electrodes 110. In some cases, the output device 130 includes an electrical circuit configured to selectively output a voltage (e.g., a defibrillation shock) across the defibrillation electrodes 144. For example, the output device 130 includes a capacitor configured to store a voltage and a discharge circuit configured to discharge the voltage across the defibrillation electrodes 144. The voltage is applied over the heart of the patient 102 and depolarizes cells within the heart. The voltage may cause the heart to, at least eventually, restore a healthy heart rhythm.

The medical device 104 selectively outputs the defibrillation shock based on the ECG 118. For example, the medical device 104 only outputs the defibrillation shock in response to detecting a shockable rhythm in the ECG 118. Shockable rhythms include ventricular fibrillation (VF) and ventricular tachycardia (V-Tach). Optionally, the medical device outputs a recommendation suggesting that the defibrillation shock should be applied to the patient 102. The recommendation is based on detecting the shockable rhythm in the ECG 118. The medical device 104 can output the defibrillation shock based on receiving an input signal, which may be input by the user 106 after the recommendation is output by the medical device 104. In various examples, the medical device 104 outputs the defibrillation shock at a particular time that depends on the ECG 118. For example, the medical device 104 outputs the defibrillation shock at a time in which the rate of change of the ECG 118 is positive. In some cases, the medical device outputs the defibrillation shock based on an input signal received from the user 106 via the user input device 128.

In various implementations of the present disclosure, the electronic caliper 120 output by the medical device 104 facilitates analysis of the ECG 118 by the user 106. Unlike a physical caliper, the electronic caliper 120 is suitable for analyzing the ECG 118 displayed on the screen of an electronic device, such as the medical device, the wearable device 132 of the patient 102, the wearable device 134 of the user 106, the mobile device 136, the computing device 138, or the display device 140.

Figure 2:
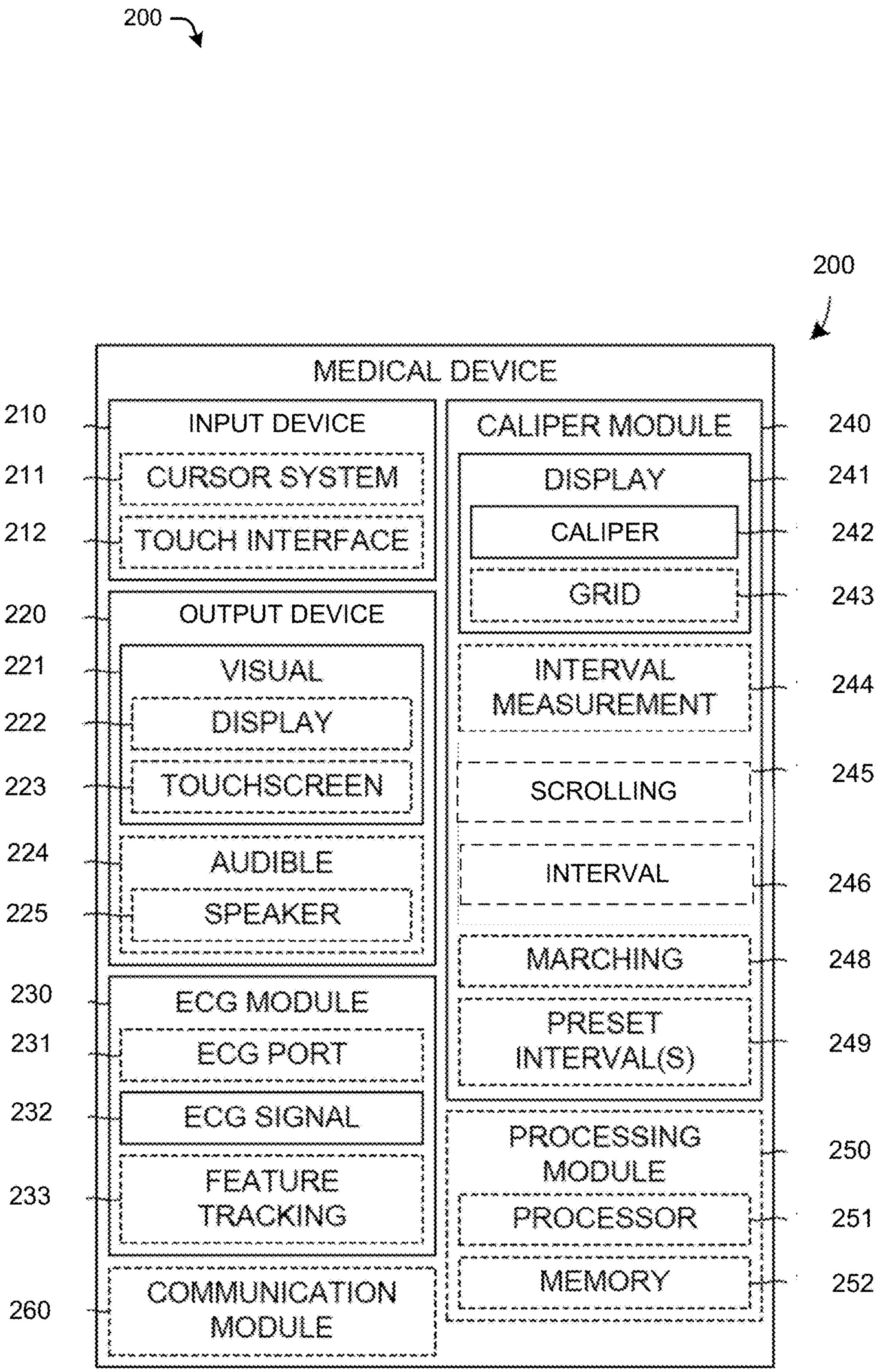
FIG. 2 illustrates an example medical device configured to output an electronic caliper.

FIG. 2 illustrates an example medical device 200 that can display an electronic caliper 242 on an ECG signal 232. In various examples, the medical device 200 is configured to manipulate the electronic caliper 242 is, such as to measure various distances (e.g., times), along the ECG signal 232. Examples of the medical device 200 include a patient monitor, a defibrillator, an automated external defibrillator (AED), a monitor-defibrillator, and other medical devices. In various examples, the medical device 200 includes an input device 210, an output device 220, an ECG module 230, a caliper module 240, a processing module 250, and a communication module 260. The ECG module 230 receives data from one or more ECG sensors and causes an ECG signal 232 to be displayed by the output device 220. An electronic caliper 242 is displayed on the ECG signal 232 by the caliper module 240 and a measurement of the interval between tips of the electronic caliper is made, which assists the user with measuring a distance or time between features of the ECG signal 232. The electronic caliper 242 is moveable along the ECG signal 232. In some cases, the ECG signal 232 is moveable relative to the electronic caliper 242. Moving the electronic caliper 242 and/or the ECG signal 232 can allow the user to compare the interval of the electronic caliper 242 to different features and/or instances of the ECG signal 232.

The input device 220 includes various interfaces, such as a physical interface, an electronic interface, or combination thereof, to allow the user to interact with the medical device 200. Using the input device 220, the user operates and/or accesses one or more features or systems of the medical device 200. For example, a cursor system 211, a touch interface 212, buttons, switches, or combination(s) thereof, are included on the medical device 200 as the input device 220.

The output device 220 is configured to relay information from the medical device 200 to the user. The output device 220 includes a visual output device 221 and/or auditory output device 224. For example, the visual output device 221 includes a display 222 and/or a touchscreen 223 that outputs the information as a visual signal. In some cases, the touchscreen 223 is included in and/or integrated with the touch interface 212 included in the input device 220 for the medical device 200. In some cases, a user inputs a signal to the medical device 200 via the touchscreen 223 by selecting and/or manipulating items displayed by the touchscreen 223. The auditory output device 224 includes, for example, a speaker 225 that provides an audible signal that is heard by the user. Examples of the audible signal include instructions regarding treatment of a patient or other indications patient data including physiological parameter values that are outside of a pre-determined range. The patient data is acquired and/or sensed by the medical device 200.

The ECG module 230 includes an ECG port 231 that is coupled to one or more sensors (e.g., electrodes) that are placed on a patient. The signals from the one or more sensors can be processed and/or displayed as an ECG signal 232. The ECG signal 232 is displayed on the visual output device 222 and is indicative of the electrical activity associated with a patient's heart. The ECG signal 232 includes a single signal (e.g., a voltage signal obtained from a single pair of electrodes) or multiple signals (e.g., voltage signals obtained from multiple pairs of electrodes, such as electrodes corresponding to a multi-lead ECG), for example. The acquired ECG signal 232 includes various features or characteristics, such as QRS complexes, RR intervals, QT intervals, other features or characteristics, or combinations thereof. A feature tracking module 233 of the ECG module 230 processes and analyzes the ECG signal 232 to identify one or more features or characteristics of the ECG signal 232. These features can be optionally labeled on the display of the ECG signal 232 in response to a user input signal (e.g., received by the input device 210) indicating such labeling or identification of one or more of the features of the ECG signal 232. In some examples, the feature tracking module 233 identifies multiple instances of the same feature, such as multiple QRS complexes of the ECG signal 232.

The caliper module 240 controls the functions and features associated with displaying and/or manipulating the electronic caliper 242 displayed with the ECG signal 232. The display functionality 241 of the caliper module 240 includes the electronic caliper 242 and a grid 243. The displayed electronic caliper 242 includes multiple visual representations (e.g., GUI elements) that are selectable by a user and displayed. According to various examples, the user interacts with the input device 210, such as the touch interface 212 or touchscreen 223, to select and/or move the electronic caliper 242 with respect to the ECG signal 232. The user also interacts with the input device 210 to select and/or move portions of the electronic caliper 242, such as one or both electronic tips of the electronic caliper 242.

The displayed electronic caliper 242 includes a first tip and a second tip that define an interval 246 extending between the two tips. The tips are moved and/or positioned with respect to the ECG signal 232 by a user using the input device 210, in various implementations. For example, the user positions the first tip of the electronic caliper 242 at a beginning point of a feature (e.g., a particular instance of the feature) of the ECG signal 232 and the second tip at an ending point of the feature (e.g., the particular instance of the feature). The interval 246 defined by the electronic caliper 242 is the length and/or duration of the feature, according to some examples.

In some cases, to position the electronic caliper 242 on the ECG signal 232, the user uses the feature tracking module 233 to select a feature and/or interval of the displayed ECG signal 232 on which the electronic calipers 242 are positioned. The grid 243 is displayed on and/or with the ECG signal 232 and allows a user to measure or estimate the length (e.g., duration) of features and/or intervals of the ECG signal 232 using the gridlines of the grid. In some cases, the gridlines are separated by distances corresponding to a scale of the grid 243. Optionally, the grid 243 is referenced to (e.g., overlaps) a tip of the electronic caliper 242. For example, the user positions the electronic caliper 242 and the gridlines of the grid 243 are positioned based on the position of the electronic caliper 242. In some cases, a gridline extends from, or is otherwise referenced to, a tip (e.g., the first tip) of the electronic caliper 242. In some examples, the grid 242 allows the user to estimate a length (e.g., a duration) of the interval 246 extending from the first tip to the second tip. In various cases, the grid 243 facilitates a visual comparison between the length (e.g., duration) of one instance of a feature to another instance of the feature in the ECG signal 232.

The interval 246 defined by the electronic caliper 142 is measured to determine an interval measurement 244. The interval measurement 244 is a numerical value indicative of a time interval and/or distance defined between the first and second tips of the calipers 242. For example, the ECG signal 232 is displayed along a time axis and the interval measurement 244 is duration spanning the interval 246 defined by the electronic caliper 242.

In some examples, the electronic caliper 242 is moved along, or repositioned relative to, the ECG signal 232 by a scrolling functionality 245. The interval 246 of the electronic caliper 242, and optionally the electronic caliper 242 itself, is moved along the ECG signal 232. In some cases, the adjustment of the interval 246 and/or the movement of the electronic caliper 242 is based on a user interaction with the input device 220. For example, the user selects and drags the interval 246 across the displayed ECG signal 232 by interacting with the touchscreen 223. Moving the electronic caliper 242 along the ECG signal 232 gives the user a visual comparison between a length (e.g., a duration) of different features and/or different instances of the same feature of the ECG signal 232. For example, the interval 246 corresponds to an initial instance of a feature, such as an RR interval in the ECG signal 232, and the electronic caliper 242 maintaining the interval 246 is moved to at least partially overlap a subsequent instance of the RR interval feature. Thus, the user can compare the length or duration of the initial instance with the subsequent instance of the same feature. For example, moving the electronic caliper 242 facilitates identifying whether the length (e.g., duration) of the feature is lengthening, shortening or staying relatively constant over time. Such comparison assists with analyzing the ECG signal 232 and patient diagnosis. For example, if the RR intervals are repeatedly irregular, the ECG signal 232 is consistent with atrial fibrillation, which may be treatable by drug therapy or synchronized cardioversion.

In some examples, the ECG signal 232 is scrolled or moved relative to the electronic caliper 242 using an ECG signal scrolling functionality 245. In some examples, a user seeks to compare the electronic calipers 242, and the interval 146 defined between the tips of the electronic caliper 242, with different instances of a particular feature of the ECG signal 232 that is not currently displayed by the display 247. To do this, the user can scroll the displayed ECG signal to cause preceding or proceeding portions of the ECG signal 232 to be displayed. The user can cause the display 222 to scroll the displayed ECG signal 232 using the ECG signal scrolling functionality 245, which causes the display 222 to output a portion of the ECG signal 232 that was not initially displayed (e.g., a preceding portion and/or a proceeding portion). By scrolling, the electronic caliper 242 is output to align with another instance of the feature with the displayed caliper 242 to assist with a visual comparison of the length, or duration, of the initial instance with the other instance.

The caliper module 240 also includes a marching functionality 248, which causes the medical device 200 to "march" (e.g., duplicate or repeat) the electronic caliper 242, and the interval 246 defined between the tips of the electronic caliper 242, across the displayed portion of the ECG signal 232. That is, the user can position the electronic caliper 242 and can select a marching feature, which causes the medical device 200 to duplicate the electronic caliper 242, along with the interval 246, across the displayed ECG signal 232. In some cases, the duplicated calipers are aligned consecutively, one after the other. in various examples, the duplicated calipers along the displayed ECG signal 232 assist with analysis of the ECG signal 232 and patient diagnosis. For example, if the duplicated calipers are aligned with regularly occurring P waves within the ECG signal 232, and the QRS complexes are asynchronous with the P waves within the ECG signal 232, the duplicated calipers facilitate a diagnosis of third-degree atrioventricular block, which is treatable by pacing. Additionally, if the displayed ECG signal 232 is scrolled by the scrolling functionality 245, the marching functionality 248 causes the caliper 242 and the interval 246 to be continued to be displayed across the newly displayed portion(s) of the ECG signal 232.

The caliper module 240 includes preset interval(s) 249 of the electronic caliper 242. For example, the user selects a preset interval 249, such as a predetermined length (e.g., duration) of the interval 246 defined between the tips of the electronic caliper 242. In an example, features of the ECG signal 232 have standard lengths (e.g., durations), and preset intervals 249 include the standard lengths. In various implementations, the user selects, using the input device 210, an appropriate preset interval 249 for the electronic caliper 242. In some cases, the user moves the electronic caliper 142 relative to the displayed ECG signal 232, or scrolls the displayed portion of the ECG signal 232, in order to compare a length (e.g., a duration) of a feature of the displayed ECG signal 232 with that of a standard length (e.g., duration) of the feature. For example, a preset interval 249 associated with an RR interval is 0.6 seconds, consistent with two-hundred RR intervals per minute. If the RR intervals within the ECG signal 232 are consistently less than the 0.6 seconds shown by the electronic caliper 242, the heart rhythm of the patient is consistent with some type of tachycardia. As a further example, the preset interval associated with an RR interval is 2.2 seconds, consistent with 50 RR intervals per minute. If the RR intervals within the ECG signal 232 are consistently longer than the 2.2 seconds shown by electronic caliper 242, the heart rhythm of the patient is consistent with some type of bradycardia.

The processing module 250 includes a processor 252 and memory 252. The memory 252 stores and instructions for operating functions and features of the medical device 200, such as controlling or assisting the functionality of the input device 220, output device 220, the ECG module 230, the caliper module 240, or any combination thereof. Additionally, the memory 252 can store patient data, such as ECG signal 232 and user configurations of the medical device 200, such as a user configuration of one or more settings of one or more functions and features of the medical device 200. In various examples, the processor 252 executes the instructions, thereby performing at least some of the functions and features of the medical device 200.

The communication module 260 is configured to communicate, unidirectionally or bi-directionally, with an external device or system. This can allow the medical device 200 to transmit information and data, such as the ECG signal 232, and receive information, such as the ECG signal 232, from an external device or system. In various implementations, the communication module 260 includes software and hardware, to communicate with an external device or system using one or more communication protocols or interfaces, such as the Internet, WI-FI®, WIGIG®, BLUETOOTH®, or other communication protocols or interfaces. For example, the medical device 200 receives the ECG signal 232 from an external device for analysis or can provide the ECG signal 232 to an external device or system for storage, such as for post-event review and analysis.

Figure 3:
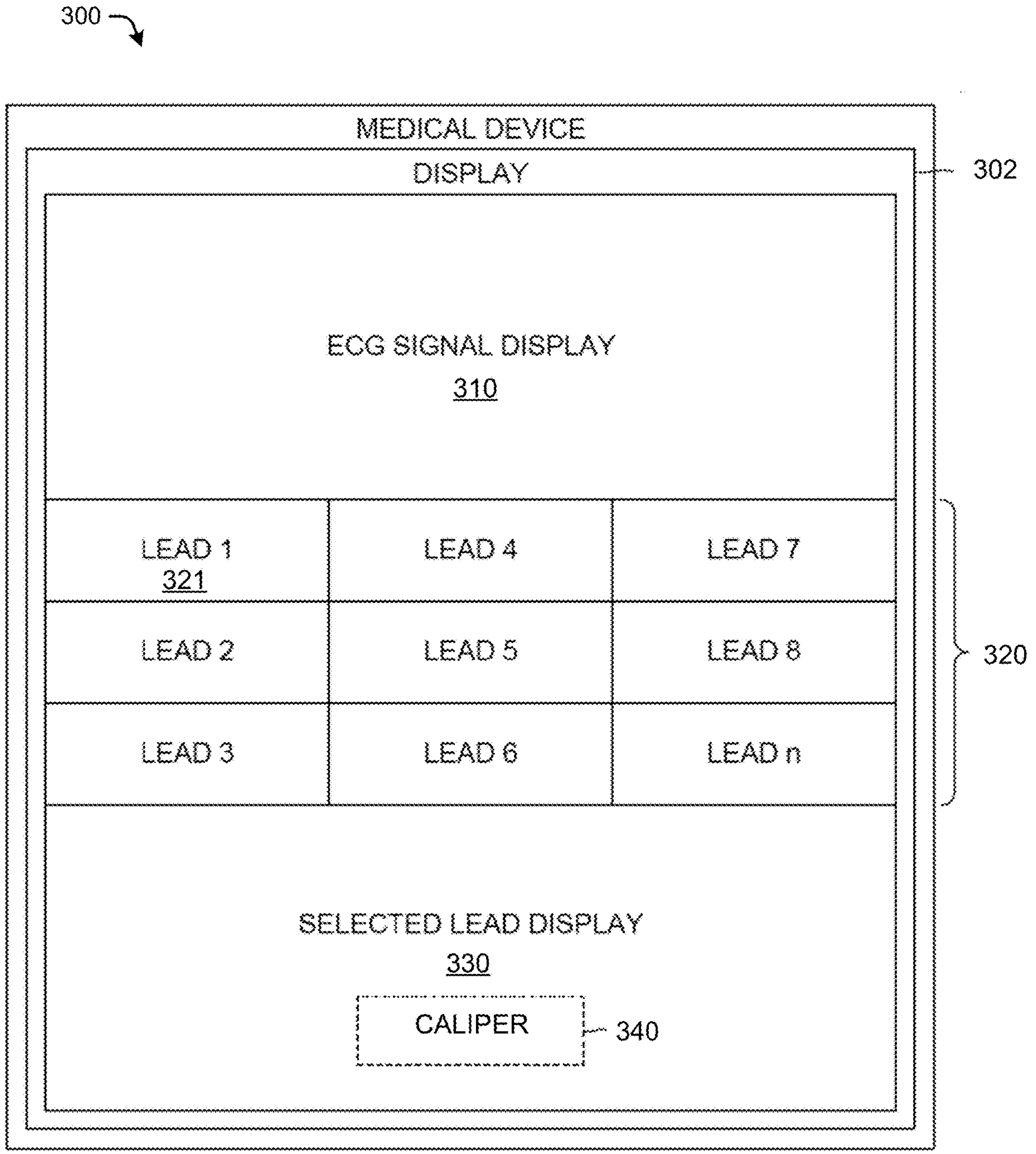
FIG. 3 illustrates another example medical device outputting an electronic caliper.

FIG. 3 is another example of a medical device 300 having electronic caliper capabilities. The medical device 300 includes a display 302 that displays various information regarding a patient. In some cases, the display 302 can is an input device, such as a touchscreen, configured to allow a user to interact with items or information displayed on the display 302. In the example shown in FIG. 3, the display 302 is divided into portions to show various information and data. For example, the portions include an ECG signal display 310, an individual display 320, and a selected lead display 330.

The ECG signal display 310 is configured to display an ECG signal of a patient. The ECG signal can be acquired (e.g., sensed), using one or more sensors. The sensor(s) include electrodes that are placed at different locations on the patient. In some examples, additional patient information, such as heart rate, blood pressure, oxygen saturation, and other physiological parameters, are additionally displayed in the ECG signal display 310 alongside the ECG signal. For instance, the additional information is displayed as within and inset or frame of the ECG signal display 210. This can allow the user to quickly view the ECG signal of the patient and other patient information together, such as to provide a more comprehensive overview of the condition of the patient.

In some examples, the ECG signal displayed by the ECG signal display 310 is a single plot from a multi-lead ECG signal. The signals 321 from the individual leads are displayed in respective portions of the individual display 320. The signals 321 output by the individual display 320 are synchronized with the ECG signal displayed in the ECG signal display 310, such that the ECG signal displayed by the ECG signal display 310 is time-aligned with the signals 321 of the individual leads displayed in the individual display 320. A user can select one of the individual lead signals 321 from the individual display 320, and the medical device 300 may display the selected lead signal in the selected lead display 330 of the display 302. When a particular lead signal 321 from the individual display 320 is selected for the selected lead display 330, a particular length (e.g., duration) of the signal is displayed by the selected lead display 330. The particular length is predetermined or selected by the user. That is, in some cases, the user selects an individual lead signal 321 and a ten-second portion of the selected individual lead signal 321 is displayed by the selected lead display 330. In some cases, the selected lead signal 321 displayed by the selected lead display 330 is frozen, and the lead signals 321 displayed in the individual display 320 are continuously updated as additional data is received by the device 300. In various cases, the lead signals 321 displayed in the individual display 320 are displayed with the same time-alignment, the same time-alignment as the signal displayed by the ECG signal display 310, or a combination thereof.

In some cases, the frozen lead signal displayed on the selected lead display 330 is analyzed using an electronic caliper 340, which can be positioned on the selected lead display 330 to measure, or assess, a length or duration of a feature of the ECG signal displayed by the selected lead display 330. In various examples, the electronic caliper 340 is moved along the displayed ECG signal, the displayed ECG signal is moved relative to the electronic caliper 240, or a combination thereof. The electronic caliper 340 facilitates comparing a length (e.g., duration) of a feature in the displayed ECG signal to a length (e.g., duration) of another feature in the displayed ECG signal. The electronic caliper 340 also facilitates comparing a length (e.g., duration) of a first instance of a particular feature in the displayed ECG signal to a second instance of the particular feature in the displayed ECG signal.

Figure 4A:
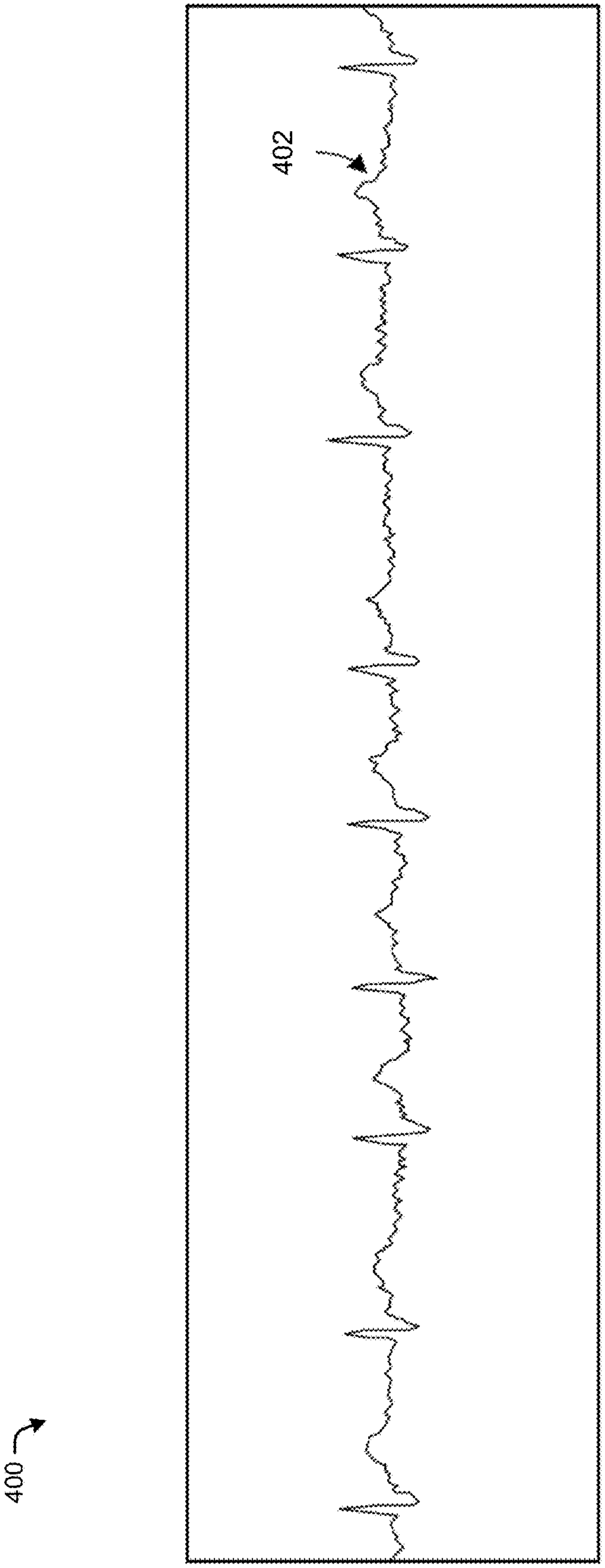
FIGS. 4A-4E illustrate examples of an electronic ECG signal displayed with an electronic caliper.

FIGS. 4A-4E illustrate examples of electronic calipers output with various ECGs. In FIG. 4A, a display 400 shows an ECG signal 402 of a patient, wherein the ECG signal 402 has various components and/or features, such as P waves, QRS complexes, and the like. Analysis of the ECG signal 402, such as measurements of or between various features of the ECG signal 402, can be used to diagnose the patient with a medical condition.

Figure 4B:
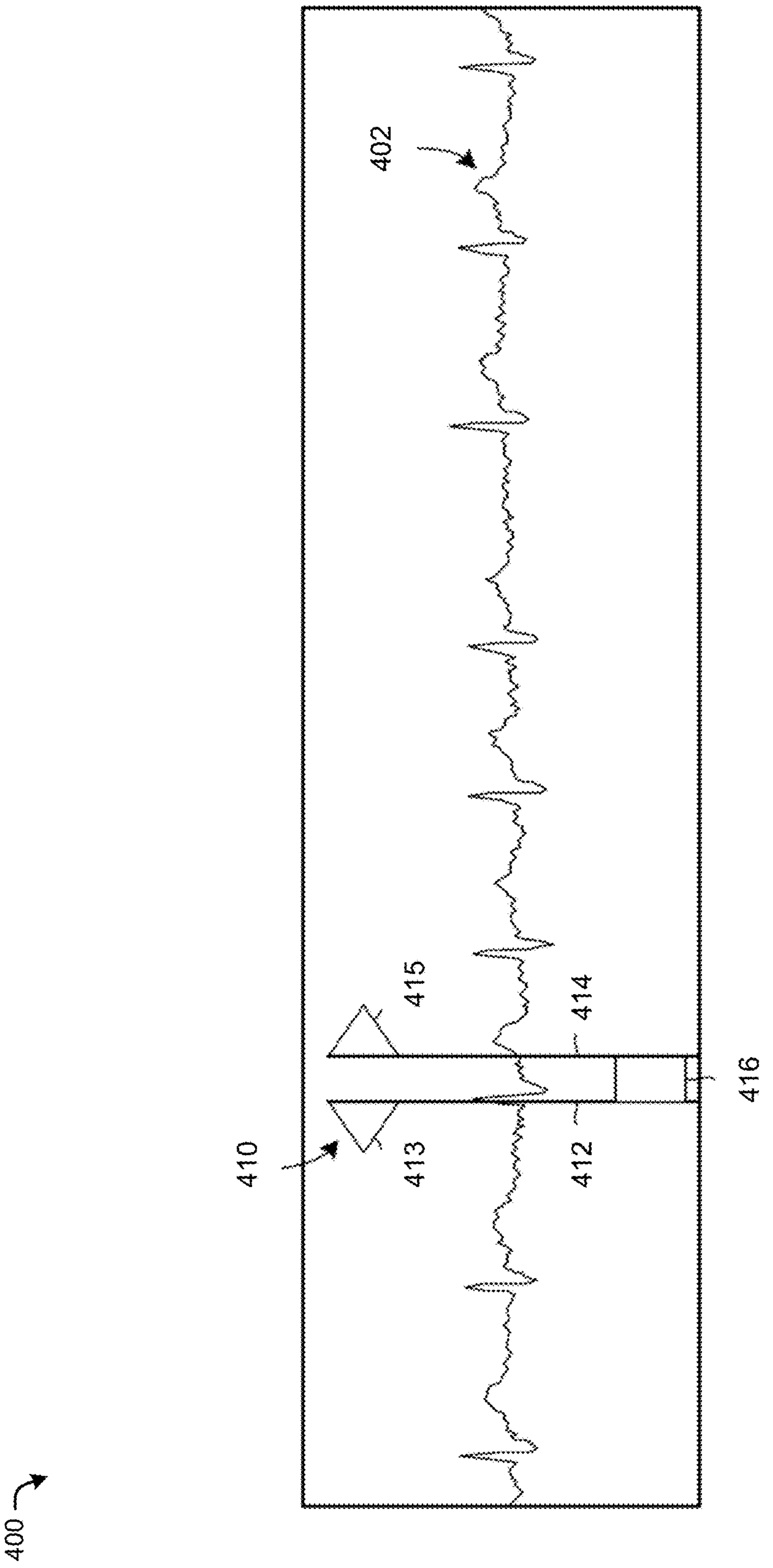

In FIG. 4B, an electronic caliper 410 is displayed on the display 400 with the ECG signal 402. For instance, the electronic caliper 410 is overlaid on and/or intersects with the ECG signal 402. The electronic caliper 410 includes a first tip 412 and a second tip 414. The electronic caliper 410 includes a spacer 416 (represented as a rectangular user interface element) that spans between the first tip 412 and the second tip 414. In the example shown in FIG. 4B, the electronic caliper 410 is initially displayed at a default position along the ECG signal 402. In some examples, the spacer 416 of the electronic caliper 410 has a default length (corresponding to an interval) defined between the first tip 412 and the second tip 414. However, in some examples, a user provides an input signal selecting or otherwise indicating a location at which the electronic caliper 410 is output. For example, the user input signal causes the first tip 412 to be output at a first location along the ECG signal 402, the second tip 414 to be output at a second location along the ECG signal 402, or a combination thereof. In various examples, the electronic caliper 410 is initially displayed having a preset spacing between the first tip 412 and the second tip 414, such that the spacer 416 has a predetermined length. The preset spacing is a default value or is a value that is selected by a user. The first tip 412 and the second tip 414 are pre-spaced according to the preset spacing when the electronic caliper 410 is initially displayed. In some cases, the pre-spaced electronic caliper 410 is displayed at a default position along the ECG signal 402. The default position, for example, is a center of the displayed ECG signal 402, a position to the left of the center of the displayed ECG signal 402, or the like. In some examples, the user indicates a location on the ECG signal 402 at which to place electronic caliper 410.

The electronic caliper 410 shown in FIG. 4B includes a first flag 413 and a second flag 415. The first flag 413 is connected to the first tip 412 and the second flag 415 is connected to the second tip 414. In various examples, the style of the electronic caliper 410 (e.g., the shapes of the first flag 413 and the second flag 415) can be any one of a number of various styles. In some cases, the user selects a style of the electronic caliper 410 that is output on the display 400. The user selects the style based on a preference or intended use, for example. In various examples, the user selects the style of the electronic caliper 410 from a menu, or from another type of listing of styles, using an input device. To move the electronic caliper 410, the first tip 412, the second tip 414, or a combination thereof, the user selects (e.g., using the input device) the electronic caliper 410, the first tip 412, the second tip 414, the interval 416, the first flag 413, the second flag 415, or a combination thereof. For example, the user selects the first flag 413 to move the first tip 412, the second flag 415 to move the second tip 414, the interval 416 to move the pair of the first tip 412 and the second tip 414 of the electronic caliper 410, or a combination thereof, along the ECG signal 402. In some examples, the user selects the ECG signal 402 to move the displayed ECG signal 402 itself.

Figure 4C:
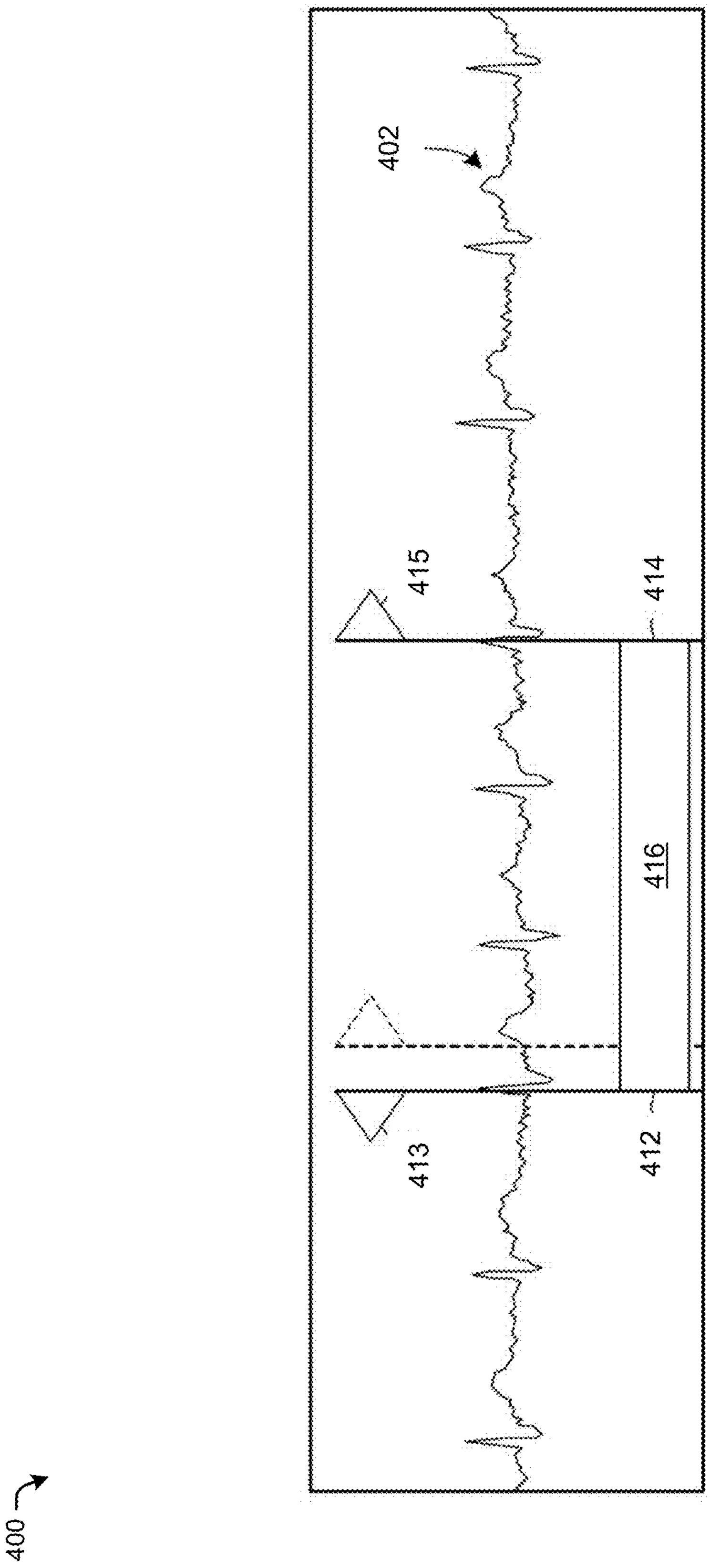

In FIG. 4C, the second tip 414 has moved from its initial location on the ECG signal 402, as indicated in dashed line, to a new location on the ECG signal 402. For example, the second tip 414 is moved by a user interacting with the second tip 414. To move the second tip 414, the user uses an input device (e.g., a touchscreen) to select the second tip 414, such as by selecting the second flag 415, and to drag the second tip 414 to the new location. In some examples, the user moves the second tip 414 from its initial location by selecting the second tip 414 and then selecting the new position on the display 400 to place the second tip 414. In some examples, the user moves the second tip 414 using a touch screen via a combination of tapping (e.g., touching) a portion of the touch screen displaying the second tip 414 and/or dragging the second tip 414 to the new location. In various examples, the user selects the second tip 414 by tapping (e.g., touching) a portion of the touch screen displaying the second flag 415. In some cases, the user presses a key (e.g., a left key or a right key) to move the second bound 414 horizontally (e.g., left or right, respectively). In some examples, the user taps or touches a portion of the touch screen displaying the second flag 415 to select it, and uses another input device, such as a knob or scroll wheel, to move the corresponding second tip 414. In various examples, the first tip 412 and/or the first flag 413 are moved in a manner similar to the second tip 414 and/or the second flag 415. The length of the spacer 416 is adjusted based on the repositioning of the first flag 413. For example, the interval between the first tip 412 and the second tip 414 is lengthened.

Figure 4D:
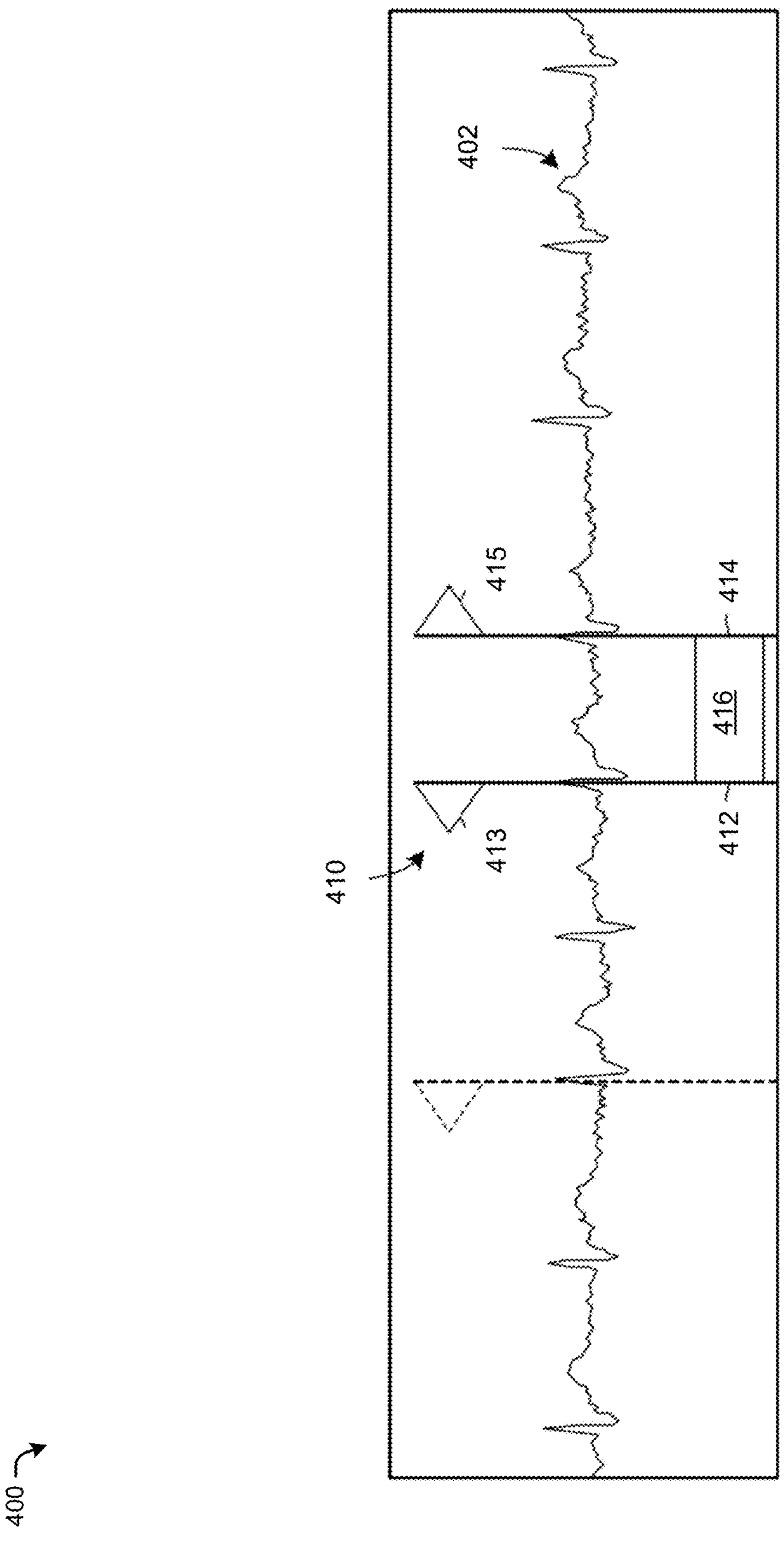

In FIG. 4D, the first tip 412 is moved from its initial location on the ECG signal 402, as indicated in dashed line, to a new location on the ECG signal 402. The first tip 412, is moved or repositioned similarly to the second tip 414. For example, the user selects the first tip 412 and/or the first flag 413 using an input device, such as a touch interface, and then moves or otherwise repositions the first tip 412 to the new location on the ECG signal 402.

Figure 4E:
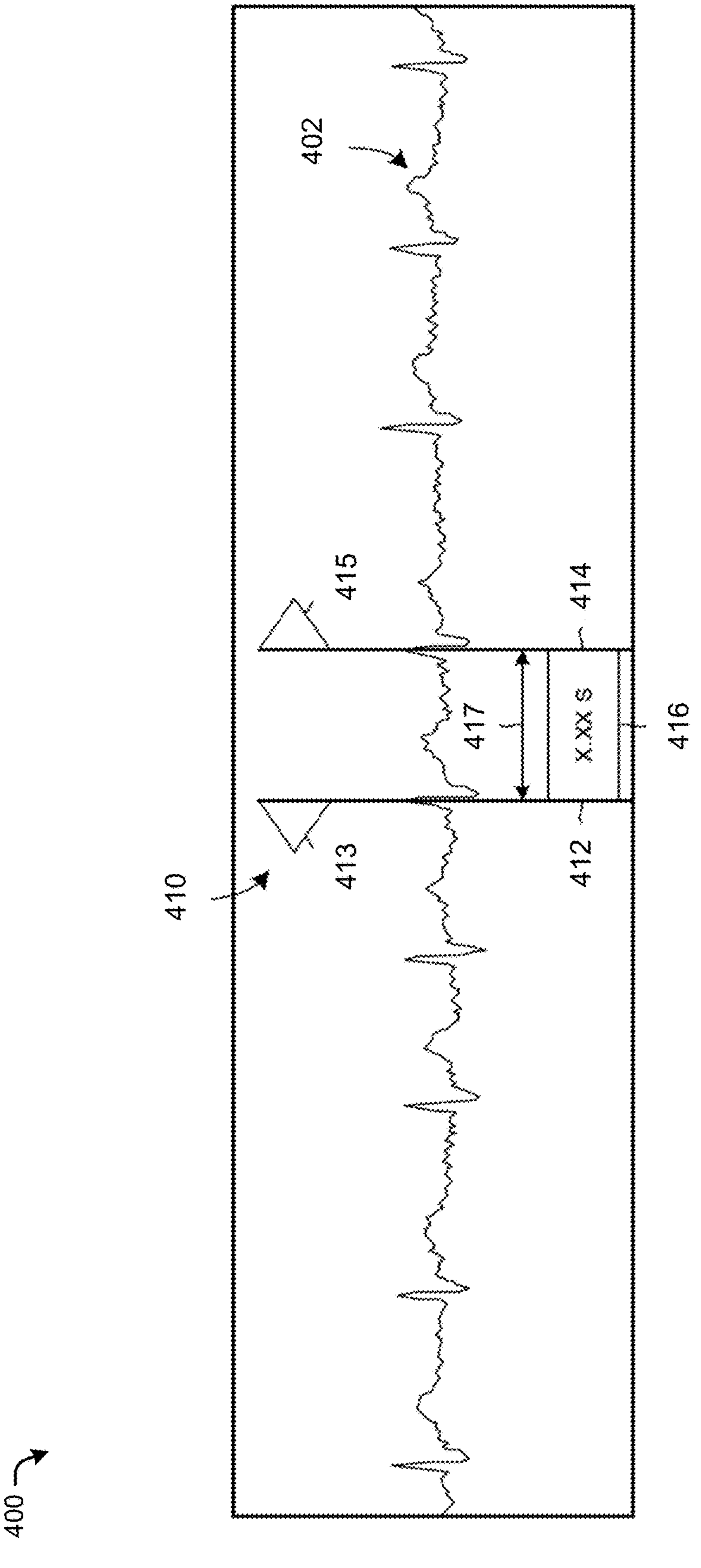

In FIG. 4E, the first tip 412 and the second tip 414 of the electronic caliper 410 have been positioned and first tip 412 and the second tip 414 are separated by an interval 417. The interval 417 is measured or otherwise determined, in some cases. For example, a time period corresponding to the interval 417 is determined. An indication of the interval 417 is displayed on the display 400. For example, the spacer 416 positioned between the first tip 412 and the second tip 414 includes the indication (e.g., a measurement) of the interval 417. The units of the indication of the interval 417 are based on the units defined along the horizontal axis of the ECG signal 402, which represents time or distance. In the example of FIG. 4E, the duration corresponding to the interval 417 is shown in seconds(s) within the spacer 416. By interacting with the electronic caliper 410, in some implementations, a user can place the first tip 412 and the second tip 414 at various points of interest on the ECG signal 402. The medical device identifies a length of or an interval between the points of interest of the ECG signal 402, based on the positions of the first tip 412 and the second tip 414. An indication (e.g., measurement) of the time period represented between the points of interest of the ECG signal 402 are determined and output by the medical device, for example. In some cases, this indication is used as part of an analysis of the ECG signal 402, such as for patient diagnosis.

FIGS. 4A-4E illustrate examples in which electronic caliper 410 is displayed and positioned on an ECG signal 402, to allow the interval 417 between points-of-interest in the ECG signal 402 to be visualized and/or measured. If the user wants to measure time intervals between other points-of-interest (e.g., between the beginnings and ends of features, instances of a feature, or the like) in the ECG signal 402, the user repositions the electronic caliper 410 by interacting with one or more input devices. In some examples, the user may wish to compare the interval 417 associated with a first instance of a particular feature of the ECG signal 402 to a second instance of the particular feature of the ECG signal 402. For example, the user compares the duration of a first RR interval to the duration a second RR interval in the ECG signal 402. To assist the user with such comparison, the user moves the electronic caliper 410 with respect to the ECG signal 402, or moves the ECG signal 402 with respect to the electronic caliper 410, to allow the user to empirically and/or visually compare the duration of the first RR interval to the duration of the second RR interval.

Figure 5:
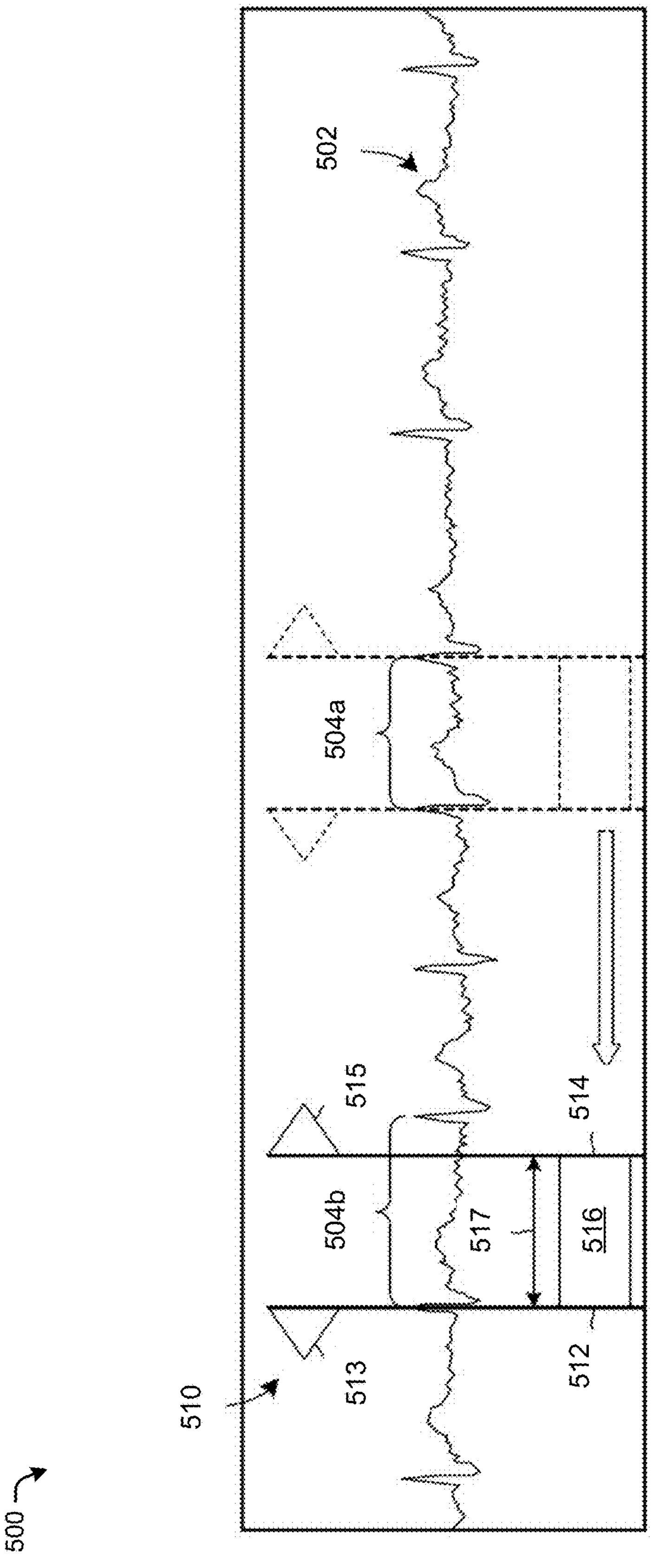
FIG. 5 illustrates an example of moving an electronic caliper along an electronic ECG signal.

FIG. 5 illustrates an example of relocating, or repositioning, an electronic caliper 510 from a first location to a second location on an ECG signal 502. A display 500 displays the ECG signal 502 and the electronic caliper 510. A user positions the electronic caliper 510 at an initial location on the ECG signal 502. The electronic caliper 510 includes a first tip 512 and a second tip 514. The first tip 512 overlaps and/or intersects a first point-of-interest in the ECG signal 502 and the second tip 514 overlaps and/or intersects a second point-of-interest in the ECG signal 502. A spacer 516 (e.g., a rectangular user interface element) is disposed between the first tip 512 and the second tip 514. An interval 517 between the first tip 512 and the second tip 514 corresponds to a distance (e.g., duration) between the first point-of-interest and the second point-of-interest.

In various examples, the user repositions (e.g., moves) the electronic caliper 510 from a first position to a second position. The interval 517 is retained when and after the electronic caliper 510 is repositioned. This can allow the user to compare the durations of different features, or instances of features, within the ECG signal 502. For example, the user uses the electronic caliper 510 to identify a first interval, such as a first RR interval 504*a* in the ECG signal 502. The interval 517 of the electronic caliper 510 corresponds to the first RR interval 504*a*. In some cases, the user repositions the electronic caliper 510 by selecting the spacer 516 positioned between the first tip 512 and the second tip 514 of the electronic caliper 510 and moving the selected electronic caliper 510 to another location on the ECG signal 502. In various cases, the electronic caliper 510 is repositioned to at least partially overlap a second RR interval 504*b*. The user can then be provided a visual comparison between the lengths of the first and second RR intervals 504*a* and 504*b* at two different locations on the ECG signal 502. Such a comparison can allow a user to quickly assess if a feature (e.g., the RR intervals) within the ECG signal 502 is lengthening, shortening, or remains relatively constant over time. Such a comparison enables the user to assess whether the feature of the ECG signal 502 is regular (e.g., nonvariant) or irregular (e.g., variant) over time. Identifying whether the feature changes in the ECG signal 502 facilitates the user with diagnosing the patient. For example, the change between the first and second RR intervals 504*a* and 504*b* indicates an arrhythmia, such as atrial fibrillation, for which a treatment may be indicated.

In various examples, the display 500 displays a predetermined segment of the ECG signal 502, such as a fixed time period of the ECG signal 502. In some cases, the user is provided an option to scroll the ECG signal 502, allowing the user to move the electronic caliper 510 to locations that precede or proceed the segment of the ECG signal 502 that is initially displayed on display 500. To scroll to another segment of the ECG signal 502, the user moves the electronic caliper 510 to the far sides of the display 500. For example, when the electronic caliper 510 is moved within a predetermined distance of a right edge of the display 500, the display 500 scrolls the displayed ECG signal 502 to the left, such that the portion of the ECG signal 502 that is displayed includes a later portion (i.e., a proceeding portion) of the ECG signal 502 than the portion that was initially displayed. In some examples, when the electronic caliper 510 is moved within a predetermined distance of a left edge of the display 500, the display 500 scrolls the displayed ECG signal 502 to the right, such that the portion of the ECG signal 502 that is displayed includes an earlier portion (i.e., a preceding portion) of the ECG signal 502 than the portion that was initially displayed. Moving the electronic caliper 510 to either of the far sides of the display 500 causes the ECG signal 502 to be scrolled. In another example, the user uses an input device to scroll to other portions of the ECG signal 502. For example, the user interacts with a user interface element output by a touchscreen including the display 500, or with some input device within a medical device, to scroll the ECG signal 502.

In some examples, the scale of the display 500 is altered. For example, the user selects a scale of the display 500 to adjust the amount of the ECG signal 502 that is shown on the display 500. For example, the user adjusts the time interval of the display 500, so that the display 500 shows additional or fewer portions of the ECG signal 502. In some cases, the user selects a shorter time interval to "zoom in" on the ECG signal 502, thereby causing the display 500 to display a shorter time interval of the ECG signal 502 than was previously displayed. In some implementations, this allows the user to more accurately position the electronic calipers 510 and provides the user with more granular detail regarding the ECG signal 502. In some examples, the user selects a longer time interval to "zoom out" on the ECG signal 502, thereby causing the display 500 to display a longer time interval of the ECG signal 502 than was previously displayed. The longer time allows the user to view an increased number of repeated features of the ECG signal 502, such as more QRS complexes than were previously displayed. The longer time interval can provide the user additional information regarding changes in various features of the ECG signal 502 over a longer period of time. The interval 517 is maintained as the view of the ECG signal 502 is adjusted, in some cases. That is, the user can interact with and set the electronic caliper 510 on a first time scale of the display 500 and, if the user changes the time scale of the display 500, the electronic caliper 510 will scale accordingly to maintain the interval 517 on the changed time scale. In this manner, if the display 500 zooms in the ECG signal 502 such that the display 500 outputs a shorter segment of the ECG signal 502, the interval 517 of the electronic caliper 510 is scaled with displayed ECG signal 502. The more detailed view of the shorter time interval provides the user greater resolution to position the electronic caliper 510, the first tip 512, the second tip 514, or a combination thereof. In examples wherein the display 500 zooms out the ECG signal 502 such that the display 500 outputs a longer segment of the ECG signal 502, the electronic caliper 510 is scaled with the displayed ECG signal 502. Thus, when the ECG signal 502 is zoomed in or out, the interval 517 is scaled such that the time period indicated by the interval 517 is maintained.

In various examples, the user moves the electronic caliper 510 along the ECG signal 502 to compare the interval 517 to the lengths (e.g., durations) of other features, or other instances of the same feature, of the ECG signal 502. In some cases, the alters the scale of the display 500, so that a longer or shorter segment of the ECG signal 502 is displayed. The display 500 scales the electronic caliper 510 accordingly, so that the interval 517 continues to correspond to the same time period before and after the scale of the display 500 is adjusted.

Figure 6A:
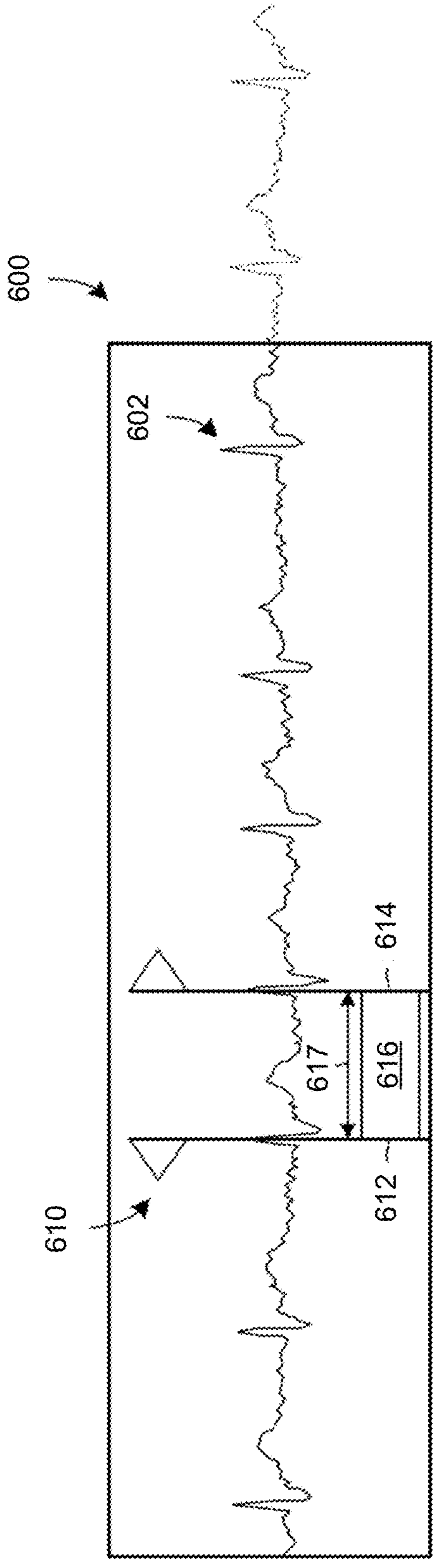
FIGS. 6A and 6B illustrate examples of moving an ECG signal relative to an electronic caliper.
Figure 6B:
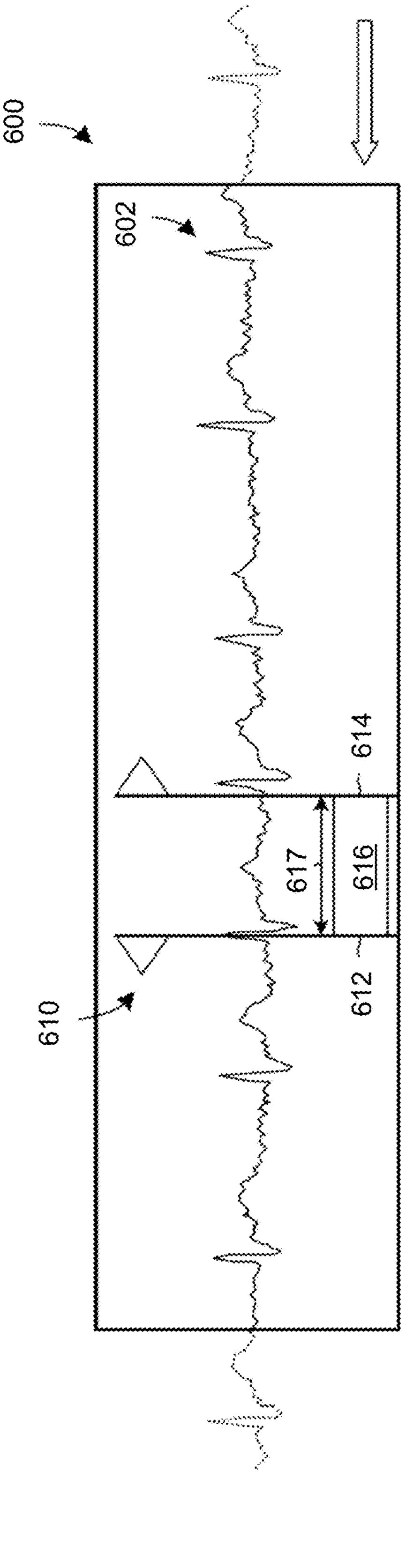

FIGS. 6A and 6B illustrate examples of moving an ECG signal 602 relative to an electronic caliper 610. The electronic caliper 610 includes a first tip 612 and a second tip 614. The first tip 612 overlaps and/or intersects a first point-of-interest in the ECG signal 602 and the second tip 614 overlaps and/or intersects a second point-of-interest in the ECG signal 602. A spacer 616 (e.g., a rectangular user interface element) is disposed between the first tip 612 and the second tip 614. An interval 617 between the first tip 612 and the second tip 614 corresponds to a difference (e.g., duration) between the first point-of-interest and the second point-of-interest.

In various examples, a user repositions the first tip 612, the second tip 614, or both, thereby adjusting the interval 617 therebetween. In some examples, the first tip 612 is positioned at the beginning of a feature in the ECG signal 602 and the second tip 614 is positioned at the end of the feature in the ECG signal 602. Thus, the interval 617 corresponds to the length (e.g., duration) of the feature. The display 600 shows a portion of the ECG signal 602. For example, a segment of the ECG signal 602 corresponding to a defined time interval is output on the display 600 with a corresponding time scale. For example, the display 600 outputs a second segment of the ECG signal 602. In some cases, the ECG signal 602 includes earlier and/or later (preceding and proceeding) portions that are not displayed on the display 600. To compare the measurement of the electronic caliper 610, or the interval 617, to other portions of the ECG signal 602, in some examples, the ECG signal 602 is scrolled, as shown in FIGS. 6A and 6B.

FIG. 6A shows the electronic caliper 610 positioned to measure the duration of a feature of the ECG signal 602. The first tip 612 is positioned to overlap and/or intersect the beginning of a first instance of the feature and the second tip 614 is positioned to overlap and/or intersect the end of the first instance of the feature, such that the interval 617 corresponds to the duration of the first instance of the feature. In various examples, to compare the interval 617 to another portion of the ECG signal 602, such as a second instance of the feature of the ECG signal 602, the display 600 scrolls the ECG signal 602 (e.g., based on direction by the user), such as shown in FIG. 6B. FIG. 6A shows the display 600 displaying an initial portion of the ECG signal 602. FIG. 6B shows the display 600 displaying a scrolled portion of the ECG signal 602 that includes a segment of the ECG signal 602 that is not included in the initial portion of the ECG signal 602. For example, FIG. 6B illustrates the display 500 outputting a segment of the ECG signal 602 corresponding to a later time period than the time period corresponding to the portion of the ECG signal 602 output by the display 600 in FIG. 6A. In various cases, the user moves the ECG signal 602 relative to the electronic calipers 610. The ability of the user to compare the interval 617 corresponding to the duration of the first instance of the feature to the duration of the second instance of the feature provides information regarding the lengthening or shortening of repeated instances of the feature in the ECG signal 602 over time. This comparison facilitates diagnosing a patient.

The examples illustrated in FIGS. 5, 6A, and 6B illustrate how electronic calipers facilitate comparing the duration of different features, or instances of a feature, within an ECG. As mentioned, this comparison assists with diagnosing a patient based on whether the feature or features are shortening, lengthening, or remaining the same over the course of the ECG signal. The examples of FIGS. 5, 6A, and 6B can be used separately or in conjunction with each other to allow users or systems to use electronic calipers to compare the duration of various features and/or instances of features in ECG signals. In some examples, an electronic caliper is positioned by moving or manipulating the tips of the electronic caliper. In some cases, the interval defined between the tips of the electronic caliper is adjusted by repositioning one or both of the times. According to some examples, the electronic caliper is repositioned, while the interval between the tips is maintained. In some cases, the ECG signal is moved relative to the electronic caliper. In various implementations, a user can compare the duration of different features and/or instances of features in the ECG signal by repositioning the electronic caliper and/or adjusting the portion of the ECG signal that is displayed.

In some cases, a feature or instance of the feature is selected. For example, the user selects the feature or instance of the feature by interacting with an input device. The electronic caliper, in some examples, is automatically positioned on the selected feature or instance of the feature. For example, a user can select or input the feature of the ECG signal, such as a QRS complex, an RR interval, or some other feature of the ECG signal, and the system can automatically display the electronic caliper on the selected feature of the ECG signal. The system and/or device displaying the ECG signal can identify the selected feature in the ECG signal by analyzing the ECG. In some cases, the displayed ECG signal includes multiple instances of the selected feature (e.g., multiple RR intervals) and the system allows the user to select a particular instance of the feature on which to display the electronic caliper. In some examples the system displays multiple electronic calipers respectively overlaying multiple instances of the selected feature.

In examples in which the electronic caliper is displayed on a single instance of the selected feature, the electronic caliper is repositionable. For example, the user is provided an option to scroll through the ECG signal or move the electronic caliper, such that the electronic caliper is overlaid onto and/or intersecting another instance of the feature. That is, the electronic caliper is displayed on an initial instance of the selected feature and repositioned to another instance of the selected feature. Repositioning the electronic caliper facilitates comparing the duration of the initial instance of the selected feature to the duration of the other instance of the selected feature. When the electronic caliper is moved along the displayed ECG signal, the interval between the tips of the electronic caliper is maintained. Thus, if the interval corresponds to the duration of the initial instance, the user can use the repositioned electronic caliper to efficiently identify how the duration of the other instance compares to the duration of the initial instance.

In some examples, the interval of the electronic caliper is automatically adjusted when the electronic caliper is moved. For example, when the electronic caliper is overlaid on or intersecting with a first instance of a particular feature, the first tip is automatically positioned at a point corresponding to the beginning of the first instance and the second tip is automatically positioned at a point corresponding to the end of the first instance, such that the interval between the first tip and the second tip corresponds to the duration of the first instance. In some examples, when the electronic caliper is moved to a second instance of the particular feature, the first tip is automatically positioned at a point corresponding to the beginning of the second instance and the second tip is automatically positioned at a point corresponding to the end of the second instance, such that the interval between the first tip and the second tip is automatically adjusted to correspond to the duration of the second feature. According to various implementations, a numerical value of the duration of the interval between the first tip and the second tip is output (e.g., displayed). The numerical value is automatically adjusted as the interval between the first tip and the second tip is adjusted. For example, when the electronic caliper is aligned with the first instance of the selected feature, a numerical value corresponding to the duration of the first instance is displayed, whereas when the electronic caliper is repositioned to a second instance of the selected feature and the interval is adjusted, the numerical value corresponding to the duration of the second instance is displayed. In this manner, the user is provided a numerical value corresponding to the interval of the electronic caliper, which provides of an empirical comparison of the duration of different features and/or instances within the ECG signal.

In various implementations, a difference between durations of the different instances of the selected feature is displayed. For example, when the electronic caliper is positioned on the first instance of the selected feature and repositioned to a second instance of the selected feature, the interval between the tips of the electronic caliper is adjusted based on the duration of the second instance of the selected feature. The difference between the duration of the first instance and the duration of the second instance is displayed as a difference (B) from the initial measurement, such as plus/minus value (±B). In some examples, the difference between the duration of the first instance and the duration of the second instance is presented as the measurement of the first instance (A) plus/minus the difference (B) between the measurement of the second instance and the first instance of the selected feature, such as A±B.

According to some implementations, the electronic caliper is positioned on the first instance of the selected feature, and when the electronic caliper is moved to the second instance of the selected feature, a third tip is added to the electronic caliper and is displayed. In some cases, the first tip is positioned at a beginning of the second instance, the second tip is positioned at an end of the second instance, and the third tip is separated from the first tip by the interval corresponding to the duration of the first instance. In this manner, the interval corresponding to the duration of the first instance of the selected feature and the interval corresponding to the duration of the second instance of the selected feature are both displayed simultaneously to provide a visual comparison of the two intervals of the selected feature. In some cases, the second tip and the third tip of the electronic caliper are displayed in different manners, such as in different intensities, styles, or weights, thereby providing a distinguishable feature between the second and third tips of the electronic caliper.

Figure 7A:
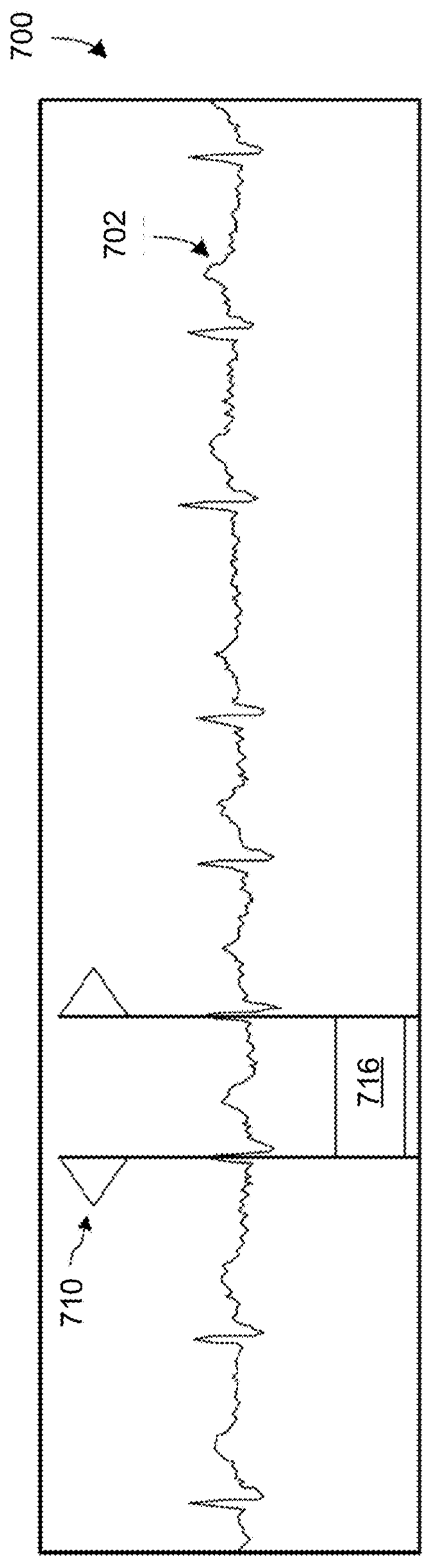
FIGS. 7A and 7B illustrate examples of displaying a grid based on a position of an electronic caliper.
Figure 7B:
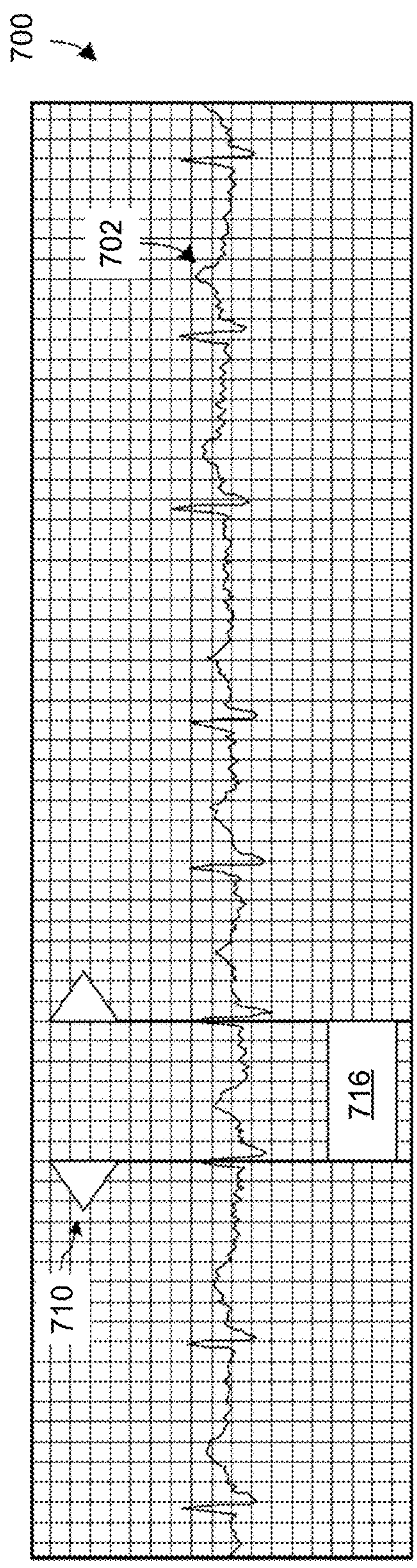

FIGS. 7A and 7B illustrate examples of a grid displayed with an electronic caliper 710 and an ECG signal 702. The ECG signal 702 is displayed by a display 700. The electronic caliper 710 is positioned on the ECG signal 702 in FIG. 7A. The electronic caliper 710 includes a first tip 712 and a second tip 714. The first tip 712 overlaps and/or intersects a first point-of-interest in the ECG signal 702 and the second tip 714 overlaps and/or intersects a second point-of-interest in the ECG signal 702. A spacer 716 (e.g., a rectangular user interface element) is disposed between the first tip 712 and the second tip 714. An interval 617 between the first tip 612 and the second tip 614 corresponds to a difference (e.g., duration) between the first point-of-interest and the second point-of-interest.

As shown in FIG. 7B, a grid is selectively displayed by the display 700, such as overlaying or underlaying the ECG signal 702. In some cases, the user selectively causes the grid to be displayed by the display 700. According to various examples, the grid has a predetermined or selected scale. For example, each box of the grid has a predetermined width and/or a width that corresponds to a predetermined time interval. In some cases, each box of the grid has a predetermined height and/or a height that corresponds to a predetermined voltage. In some cases, at least one gridline is referenced off the first tip 712 of the electronic caliper 710. For example, the horizontal scale of the displayed grid is referenced to the first bound of the electronic caliper 710 so that the vertical lines of the grid are equally spaced from an origin that overlaps the first tip 712 of the electronic caliper 710. In this arrangement, a horizontal interval (e.g., indicating a duration) from the first tip to another portion of the ECG signal 702 is efficiently discernable using the displayed grid.

In some implementations, various intervals along other portions of the ECG signal 702 (e.g., other instances of a particular feature measured by the electronic caliper 710) are estimated and/or measured using the known scale of the displayed grid. In some cases, the electronic caliper 710 is repositioned (e.g., by the user), such as by moving the electronic caliper 710 relative to the displayed ECG signal 702 and redefining the grid such that at least one vertical gridline of the grid remains referenced to the first tip 712 of the electronic calipers 710. In some cases, the grid is selectively displayed based on an input signal from a user, such as a selection of a grid on/off input button or element. In some examples, the grid is displayed by default, depending on an operating mode of the system or device displaying the ECG signal 702.

Figure 8A:
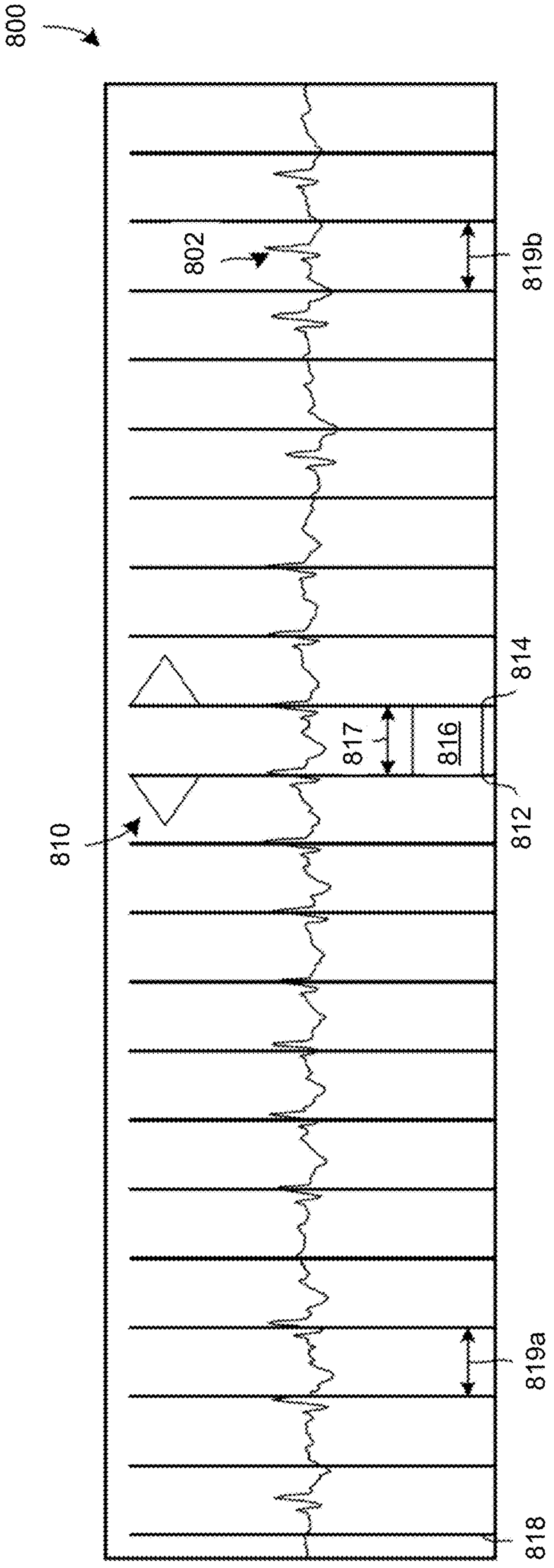
FIGS. 8A to 8C illustrate examples of displaying marching electronic calipers on an ECG signal.

FIG. 8A illustrates an example of an electronic caliper 810 displayed on an ECG signal 802 and "marching," or repeating, the electronic caliper 810 on the ECG signal 802. The ECG signal 802 is displayed by a display 800. The electronic caliper 810 includes a first tip 812 and a second tip 814. The first tip 812 overlaps and/or intersects a first point-of-interest in the ECG signal 802 and the second tip 814 overlaps and/or intersects a second point-of-interest in the ECG signal 802. A spacer 816 (e.g., a rectangular user interface element) is disposed between the first tip 812 and the second tip 814. An interval 817 between the first tip 812 and the second tip 814 corresponds to a difference (e.g., duration) between the first point-of-interest and the second point-of-interest. In some cases, a user positions the first tip 812 and the second tip 814 of the electronic caliper 810 on the ECG signal 802, thereby defining the interval 817. According to various examples, the user inputs a user input signal into an input device that causes the display 800 to "march," duplicate, or repeat, the electronic caliper 810 along the ECG signal 802. For example, the display outputs duplicated electronic calipers overlying and/or intersecting with the ECG signal 802, wherein each of the duplicated calipers includes a pair of tips separated by the same interval 817 as the original electronic caliper 810. With the marching functionality activated, the duplicated calipers are output along the ECG signal 802 relative to the electronic caliper 810. The distances between tips of the duplicated calipers, such as 819*a* and 819*b*, correspond to the interval 817 of the original electronic caliper 810. In various examples, the tips of the duplicated calipers are output as vertical lines 818, or other user interface elements. The duplicated calipers allow a user to visually identify whether features of the ECG signal 802, or instances of a feature of the ECG signal 802, are occurring at regular intervals. In some cases, the duplicated calipers illustrate the irregularity of the features and/or instances in the ECG signal 802. For example, the electronic caliper 810 defines a first RR interval. By marching the electronic caliper 810 along the ECG signal 802, the user can be provided a visual indication of the variance of the RR intervals of the ECG signal 802 over time.

With the marching functionality active, the electronic calipers 810 is adjustable. For instance, the first tip 812 and/or the second tip 814 are moved (e.g., by a user), and the lengths of the repeated intervals, such 819*a* and 819*b*, are automatically adjusted based on the newly defined interval 817. In some cases, the ECG signal 802 is scrolled, such that the display 800 outputs other portions of the ECG signal 802, and the duplicated calipers are automatically repeated on the ECG signal 802 as it is scrolled by the display 800. Similarly, if the user changes the scale of the displayed ECG signal 802, such as causing a longer or shorter duration of the ECG signal 802 to be displayed by the display 800, the duplicated calipers are automatically adjusted to continue to define the same duration on the adjusted ECG signal 802 displayed with the adjusted time scale.

Figure 8B:
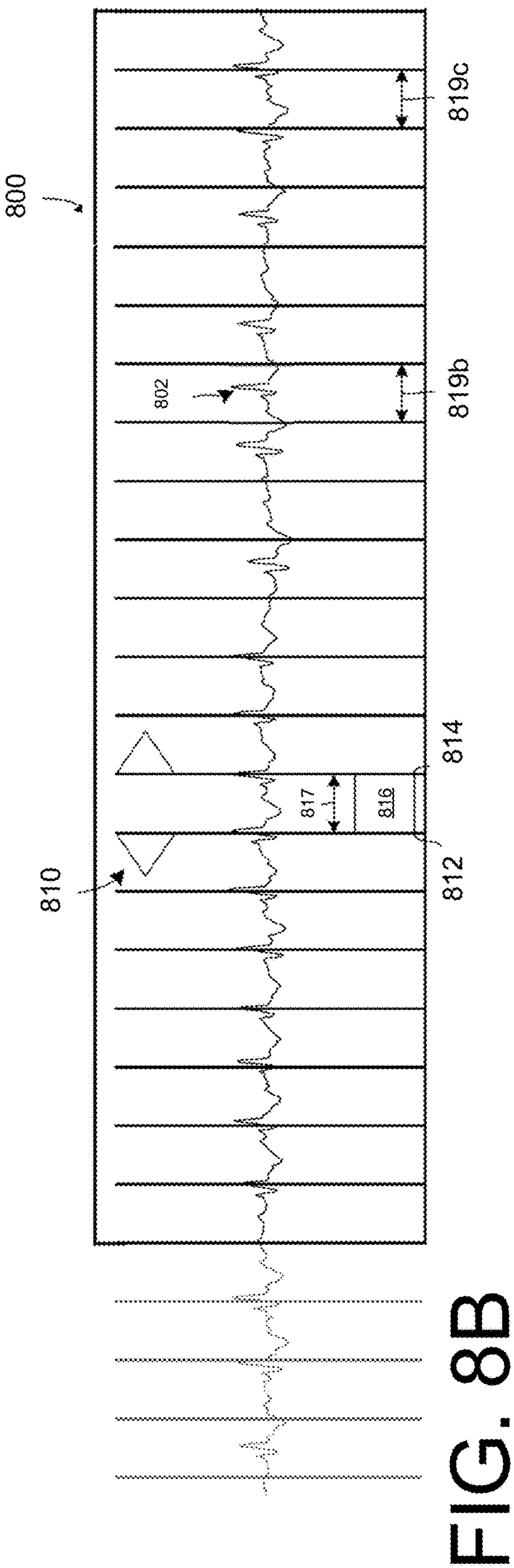

In some cases, the ECG signal 802 is scrolled with the marching functionality active. For example, FIG. 8B illustrates an example of scrolling the ECG signal 802 and the duplicated calipers, such that the duplicated calipers move with the scrolled ECG signal 802. The ECG signal 802 is scrolled, or moved, relative to the display 800. However, the first tip 812, the second tip 814, and the vertical lines 818 intersect and/or overlap the same positions of the ECG signal 802 in FIG. 8B as those indicated in FIG. 8A. Various techniques, such as those described above with reference to FIGS. 6A and 6B, are used to scroll the ECG signal 802 on the display 800. In some cases, a user input received by an input device can cause a system including the display 800 to scroll the duplicated calipers with the ECG signal 802 on the display 800.

Figure 8C:
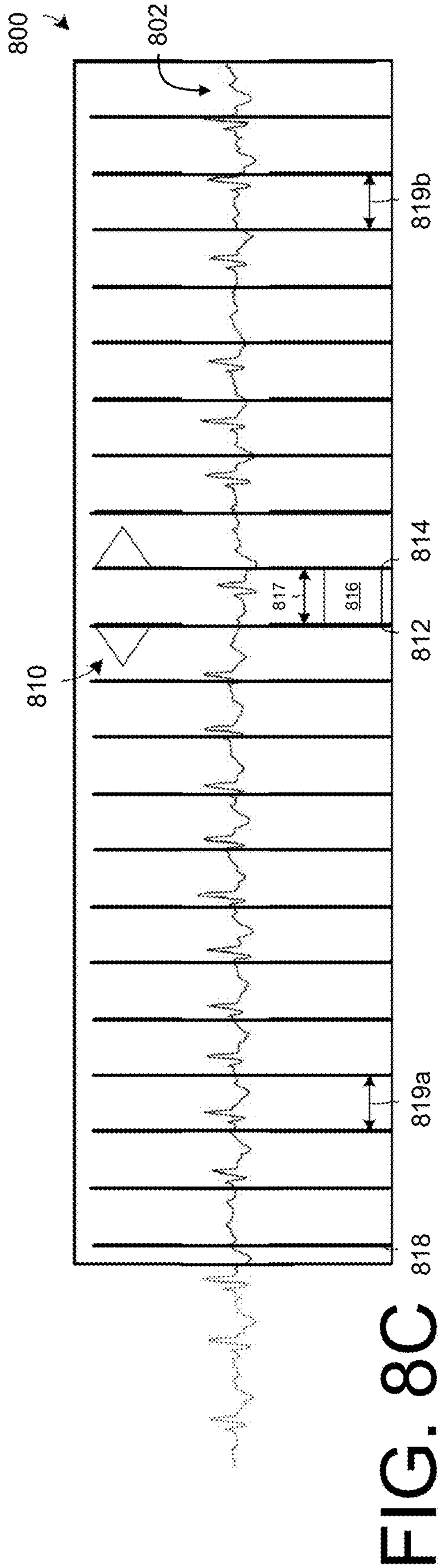

FIG. 8C illustrates an example of scrolling the ECG signal 802 while the duplicated calipers are stationary. That is, the duplicated calipers are "frozen" on the display 800 as the ECG signal 802 is scrolled. As shown, the first tip 812, the second tip 814, and the vertical lines 818 of the duplicated calipers remain at the same positions on the display 800 as those indicated in FIG. 8A. However, the ECG signal 802 is scrolled, or moved, relative to the display 800, such that the first tip 812, the second tip 814, and the vertical lines 818 intersect and/or overlap different positions of the ECG signal 802 in FIG. 8B than those indicated in FIG. 8A. Various techniques, such as those described above with reference to FIGS. 6A and 6B, are used to scroll the ECG signal 802 on the display 800. In some cases, a user input received by an input device can trigger a system including the display 800 to freeze the duplicated calipers on the display 800.

FIGS. 9-14 illustrate example methods related to various implementations of the present disclosure. Although FIGS. 9-14 illustrates separate processes, in various examples, a single entity can perform any combination of the processes. Furthermore, although each of FIGS. 9-14 illustrates steps in a particular order, implementations are not limited to the specific order of operations illustrated in the figures.

Figure 9:
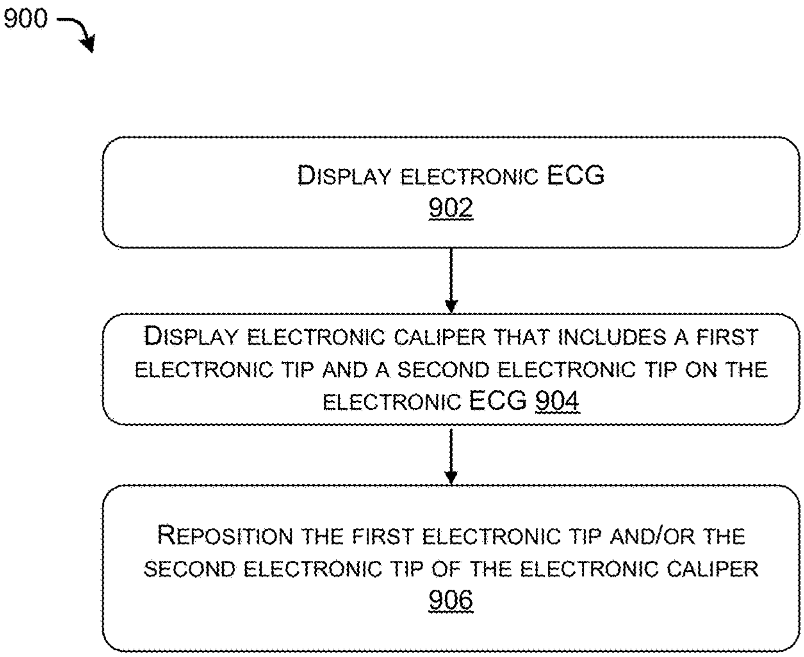
FIG. 9 illustrates an example process of displaying an electronic caliper on an ECG signal.

FIG. 9 illustrates an example process 900 for repositioning an electronic caliper. In various implementations, the process 900 is performed by an entity including the medical device 104, a processor of the medical device 104, the display 114, the wearable device 132, the wearable device 134, the mobile device 136, the computing device 138, the display device 140, or any combination thereof.

At 902, the entity displays an electronic ECG. In various examples, the electronic ECG is output on an electronic display. For example, the electronic ECG is included in a GUI output by the display. The electronic ECG illustrates an electrical activity of the heart of an individual (e.g., a patient) over time. For example, the electronic ECG includes a plot of a voltage between one or more sensor leads attached to the patient over time.

At 904, the entity displays an electronic caliper on the electronic ECG. The electronic caliper includes a first electronic tip and a second electronic tip. In various cases, the electronic caliper is output within the GUI. For example, the electronic caliper is overlaid on the electronic ECG within the GUI. In various cases, the electronic caliper intersects the electronic ECG. In some examples, the first electronic tip is overlaid and/or intersects a first point of the electronic ECG and the second electronic tip is overlaid on and/or intersects a second point of the electronic ECG. In various examples, the first point is the beginning of a feature in the electronic ECG and the second point is the end of the feature in the electronic ECG. Examples of the feature include a PR interval, a PQ segment, a QRS complex, a QT interval, an ST segment, or an RR interval. According to some cases, the first electronic tip includes a first flag and the second electronic tip includes a second flag. The first electronic tip and the second electronic tip are separated by an interval, which corresponds to the duration of the feature in some examples.

At 906, the entity repositions the first electronic tip and/or the second electronic tip of the electronic caliper. For example, the entity moves the first electronic tip and/or the second electronic tip within the GUI. In some cases, the entity receives an input signal from a user and adjusts the position of the first electronic tip and/or the second electronic tip based on the input signal. According to some examples, the entity receives an input signal from a user and adjusts the position of the electronic ECG based on the input signal, and automatically adjusts the position of the first electronic tip and/or the second electronic tip based on the adjustment to the position of the electronic ECG. An input signal is received from the user via an input device, such as one or more touch sensors integrated into a touch screen displaying the electronic ECG and/or the electronic caliper. In various cases, the first electronic tip and/or the second electronic tip is moved relative to the electronic ECG within the GUI. In some cases, the interval between the first electronic tip and/or the second electronic tip is maintained as the electronic caliper is repositioned.

In particular implementations, once the first electronic tip and/or the second electronic tip are repositioned, the electronic caliper is output on a feature of the electronic ECG (e.g., a PR interval, a PQ segment, a QRS complex, a QT interval, an ST segment, or an RR interval). For example, the user repositions the first electronic tip to be overlaid on and/or intersecting the beginning of a feature and/or repositions the second electronic tip to be overlaid on and/or intersecting the end of the feature.

In some examples, the electronic caliper is initially positioned on a first instance of a feature and is repositioned on a second instance of the feature in the electronic ECG. In some cases, the first electronic tip is overlaid on and/or intersecting the beginning of a first instance of a feature (e.g., a first RR interval) in the electronic ECG and the second electronic tip is overlaid on and/or intersecting the end of the first instance. An interval between the first electronic tip and the second electronic tip corresponds to the duration of the first instance of the feature. According to some implementations, the electronic caliper is repositioned such that the first electronic tip is overlaid on and/or intersecting the beginning of a second instance of the feature (e.g., a second RR interval) in the electronic ECG. The interval is maintained, in some cases, such that a user can efficiently identify a difference between the duration of the first instance of the feature and the second instance of the feature after the electronic caliper is repositioned.

Figure 10:
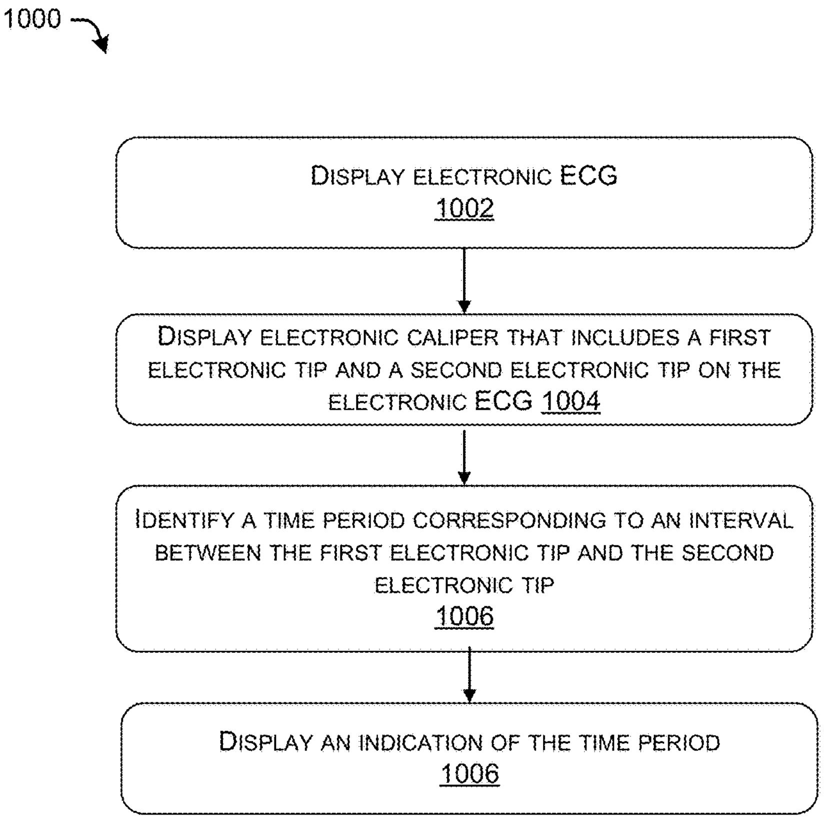
FIG. 10 illustrates an example process for measuring a time period using an electronic caliper.

FIG. 10 illustrates an example process 1000 for measuring a time period using an electronic caliper. In various implementations, the process 1000 is performed by an entity including the medical device 104, a processor of the medical device 104, the display 114, the wearable device 132, the wearable device 134, the mobile device 136, the computing device 138, the display device 140, or any combination thereof.

At 1002, the entity displays an electronic ECG. In various examples, the electronic ECG is output on an electronic display. For example, the electronic ECG is included in a GUI output by the display. The electronic ECG illustrates an electrical activity of the heart of an individual (e.g., a patient) over time. For example, the electronic ECG includes a plot of a voltage between one or more sensor leads attached to the patient over time.

At 1004, the entity displays an electronic caliper on the electronic ECG. The electronic caliper includes a first electronic tip and a second electronic tip. In various cases, the electronic caliper is output within the GUI. For example, the electronic caliper is overlaid on the electronic ECG within the GUI. In various cases, the electronic caliper intersects the electronic ECG. In some examples, the first electronic tip is overlaid and/or intersects a first point of the electronic ECG and the second electronic tip is overlaid on and/or intersects a second point of the electronic ECG. In various examples, the first point is the beginning of a feature in the electronic ECG and the second point is the end of the feature in the electronic ECG. Examples of the feature include a PR interval, a PQ segment, a QRS complex, a QT interval, an ST segment, or an RR interval. According to some cases, the first electronic tip includes a first flag and the second electronic tip includes a second flag.

At 1006, the entity identifies a time period corresponding to an interval between the first electronic tip and the second electronic tip. For example, the first electronic tip and the second electronic tip are separated in a direction that corresponds to a time axis of the electronic ECG. The first point intersecting and/or underlaying the first electronic tip is associated with a first time and the second point intersecting and/or underlaying the second electronic tip is associated with a second time. The time period is a difference between the first time and the second time, in various examples.

At 1008, the entity displays an indication of the time period. In some cases, the entity outputs the indication of the time period within the GUI. For example, the indication is overlaid on or otherwise included in a user interface element (e.g., a rectangular element) displayed between the first electronic tip and the second electronic tip. According to various examples, the indication of the time period includes the display of a numeric value corresponding to the time period. For example, the indication is displayed as a number of seconds representing the duration of the time period. In some cases in which the first electronic tip and/or the second electronic tip is repositioned, the entity adjusts the indication of the time period to correspond to the magnitude of the interval between the repositioned electronic tips.

Figure 11:
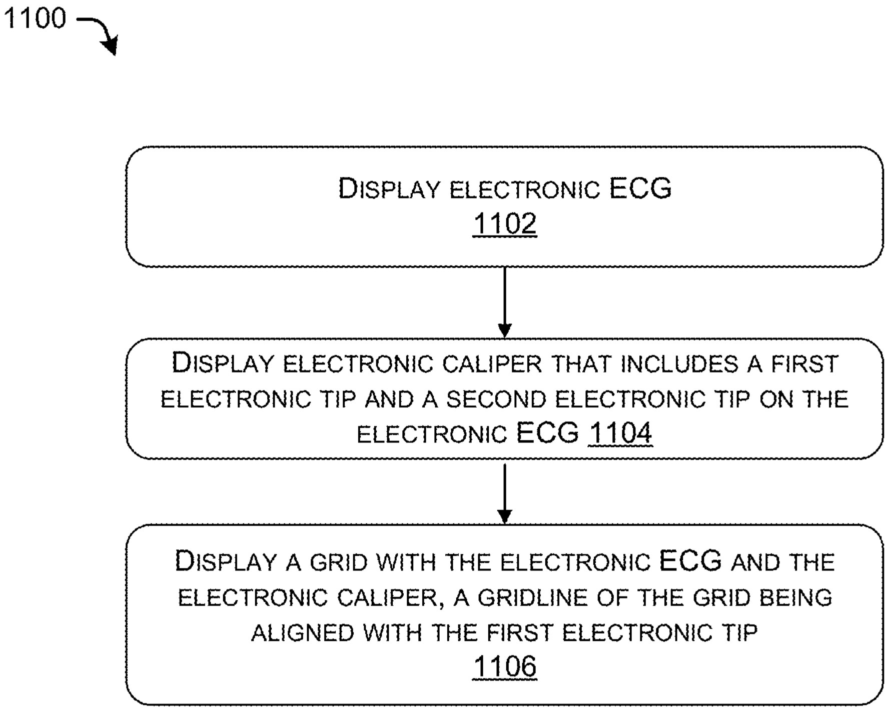
FIG. 11 illustrates an example process for displaying a grid with an electronic ECG and an electronic caliper.

FIG. 11 illustrates an example process 1100 for displaying a grid with an electronic ECG and an electronic caliper. In various implementations, the process 1100 is performed by an entity including the medical device 104, a processor of the medical device 104, the display 114, the wearable device 132, the wearable device 134, the mobile device 136, the computing device 138, the display device 140, or any combination thereof.

At 1102, the entity displays an electronic ECG. In various examples, the electronic ECG is output on an electronic display. For example, the electronic ECG is included in a GUI output by the display. The electronic ECG illustrates an electrical activity of the heart of an individual (e.g., a patient) over time. For example, the electronic ECG includes a plot of a voltage between one or more sensor leads attached to the patient over time.

At 1104, the entity displays an electronic caliper on the electronic ECG. The electronic caliper includes a first electronic tip and a second electronic tip. In various cases, the electronic caliper is output within the GUI. For example, the electronic caliper is overlaid on the electronic ECG within the GUI. In various cases, the electronic caliper intersects the electronic ECG. In some examples, the first electronic tip is overlaid and/or intersects a first point of the electronic ECG and the second electronic tip is overlaid on and/or intersects a second point of the electronic ECG. In various examples, the first point is the beginning of a feature in the electronic ECG and the second point is the end of the feature in the electronic ECG. Examples of the feature include a PR interval, a PQ segment, a QRS complex, a QT interval, an ST segment, or an RR interval. According to some cases, the first electronic tip includes a first flag and the second electronic tip includes a second flag. The first electronic tip and the second electronic tip are separated by an interval, which corresponds to the duration of the feature in some examples.

At 1106, the entity displays a grid with the electronic ECG and the electronic caliper. A gridline of the grid is aligned with the first electronic tip, the second electronic tip, or both, in some cases. According to some examples, the grid includes various boxes with a consistent height and width. The width, for example, corresponds to a particular time interval. The height, for example, corresponds to a particular voltage. Thus, the grid provides a consistent scale by which to assess various time periods and/or voltages of the electronic ECG. In some cases, the grid is selectively displayed based on an input signal received from a user.

Figure 12:
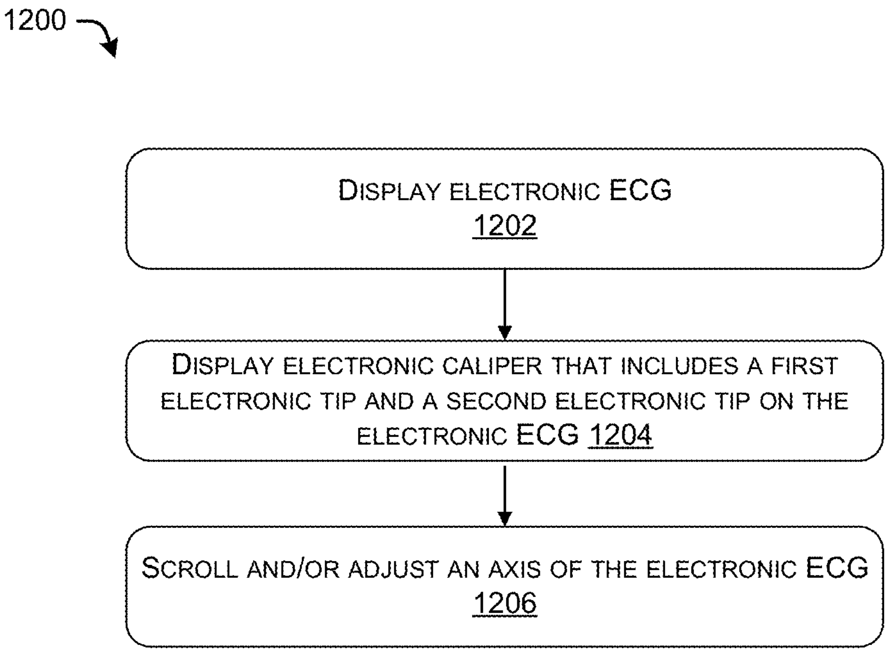
FIG. 12 illustrates an example process for adjusting the display of an electronic ECG.

FIG. 12 illustrates an example process 1200 for adjusting the display of an electronic ECG. In various implementations, the process 1200 is performed by an entity including the medical device 104, a processor of the medical device 104, the display 114, the wearable device 132, the wearable device 134, the mobile device 136, the computing device 138, the display device 140, or any combination thereof.

At 1202, the entity displays an electronic ECG. In various examples, the electronic ECG is output on an electronic display. For example, the electronic ECG is included in a GUI output by the display. The electronic ECG illustrates an electrical activity of the heart of an individual (e.g., a patient) over time. For example, the electronic ECG includes a plot of a voltage between one or more sensor leads attached to the patient over time.

At 1204, the entity displays an electronic caliper on the electronic ECG. The electronic caliper includes a first electronic tip and a second electronic tip. The electronic caliper includes a first electronic tip and a second electronic tip. In various cases, the electronic caliper is output within the GUI. For example, the electronic caliper is overlaid on the electronic ECG within the GUI. In various cases, the electronic caliper intersects the electronic ECG. In some examples, the first electronic tip is overlaid and/or intersects a first point of the electronic ECG and the second electronic tip is overlaid on and/or intersects a second point of the electronic ECG. In various examples, the first point is the beginning of a feature in the electronic ECG and the second point is the end of the feature in the electronic ECG. Examples of the feature include a PR interval, a PQ segment, a QRS complex, a QT interval, an ST segment, or an RR interval. According to some cases, the first electronic tip includes a first flag and the second electronic tip includes a second flag. The first electronic tip and the second electronic tip are separated by an interval, which corresponds to the duration of the feature in some examples.

At 1206, the entity scrolls and/or adjusts an axis of the electronic ECG. In various implementations, the entity outputs a preceding and/or proceeding portion of the electronic ECG. In some cases, the entity scrolls and/or adjusts the axis of the electronic ECG based on a user input signal.

Figure 13:
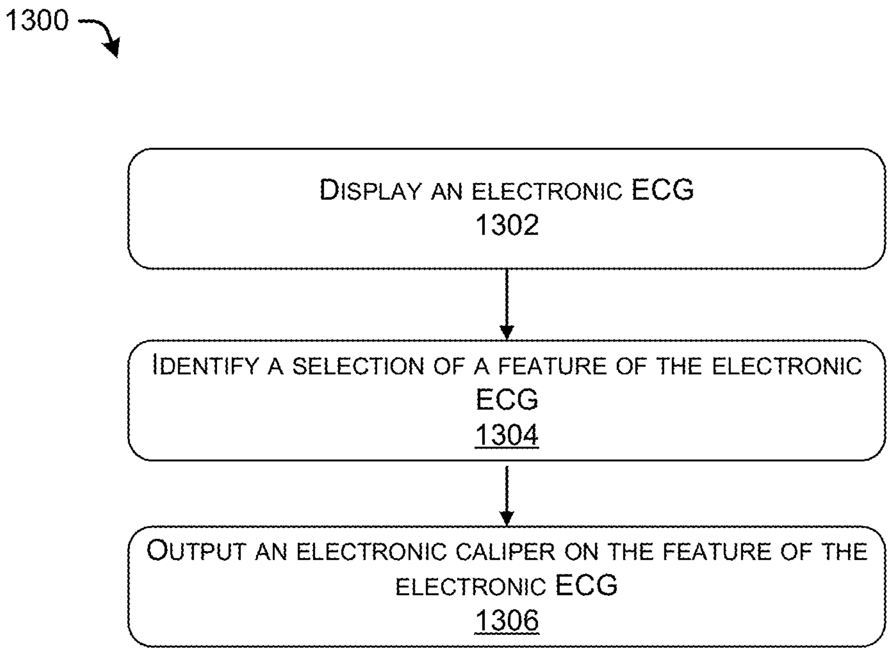
FIG. 13 illustrates an example process for automatically outputting an electronic caliper on a selected feature of an electronic ECG.

FIG. 13 illustrates an example process 1300 for automatically outputting an electronic caliper on a selected feature of an electronic ECG. In various implementations, the process 1300 is performed by the medical device 104, a processor of the medical device 104, the display 114, the wearable device 132, the wearable device 134, the mobile device 136, the computing device 138, the display device 140, or any combination thereof.

At 1302, the entity displays an electronic ECG. In various examples, the electronic ECG is output on an electronic display. For example, the electronic ECG is included in a GUI output by the display. The electronic ECG illustrates an electrical activity of the heart of an individual (e.g., a patient) over time. For example, the electronic ECG includes a plot of a voltage between one or more sensor leads attached to the patient over time.

At 1304, the entity identifies a selection of a feature of the electronic ECG. For example, the entity receives a user input signal indicates a selection of a PR interval, a PQ segment, a QRS complex, a QT interval, an ST segment, or an RR interval within the electronic ECG. In some cases, the user input signal selects the feature from a list, such as a drop-down menu within the GUI. In various examples, the user input signal selects a particular instance of the feature in the electronic ECG. According to some implementations, the entity automatically analyzes the electronic ECG and identifies the selected feature in the electronic ECG. In various examples, the entity identifies the beginning of the selected feature and the end of the selected feature in the electronic ECG. For example, if an RR interval is selected, the entity identifies the peak of a first R wave by identifying a first local maximum of the electronic ECG and the entity identifies the peak of a second R wave by identifying a second local maximum of the electronic ECG, wherein the peak of the first R wave corresponds to the beginning of the RR interval and the peak of the second R wave corresponds to the end of the RR interval.

At 1306, the entity outputs an electronic caliper on the feature of the electronic ECG. The electronic caliper includes a first electronic tip and a second electronic tip. In various cases, the electronic caliper is output within the GUI. For example, the electronic caliper is overlaid on the electronic ECG within the GUI. In various cases, the electronic caliper intersects the electronic ECG. In some examples, the first electronic tip is overlaid and/or intersects a first point of the electronic ECG and the second electronic tip is overlaid on and/or intersects a second point of the electronic ECG. In various examples, the first point is the beginning of the selected feature in the electronic ECG and the second point is the end of the selected feature in the electronic ECG. According to some cases, the first electronic tip includes a first flag and the second electronic tip includes a second flag. The first electronic tip and the second electronic tip are separated by an interval, which corresponds to the duration of the feature in some examples.

Figure 14:
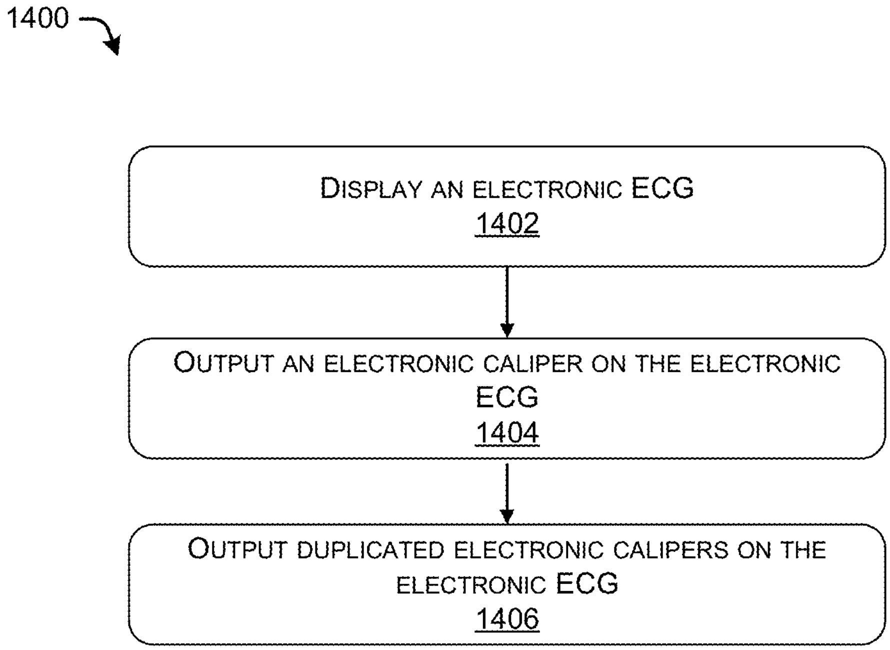
FIG. 14 illustrates an example process for duplicating an electronic caliper.

FIG. 14 illustrates an example process 1400 for duplicating an electronic caliper. In various implementations, the process 1400 is performed by the medical device 104, a processor of the medical device 104, the display 114, the wearable device 132, the wearable device 134, the mobile device 136, the computing device 138, the display device 140, or any combination thereof.

At 1402, the entity displays an electronic ECG. In various examples, the electronic ECG is output on an electronic display. For example, the electronic ECG is included in a GUI output by the display. The electronic ECG illustrates an electrical activity of the heart of an individual (e.g., a patient) over time. For example, the electronic ECG includes a plot of a voltage between one or more sensor leads attached to the patient over time.

At 1404, the entity outputs an electronic caliper on the electronic ECG. The electronic caliper includes a first electronic tip and a second electronic tip. In various cases, the electronic caliper is output within the GUI. For example, the electronic caliper is overlaid on the electronic ECG within the GUI. In various cases, the electronic caliper intersects the electronic ECG. In some examples, the first electronic tip is overlaid and/or intersects a first point of the electronic ECG and the second electronic tip is overlaid on and/or intersects a second point of the electronic ECG. In various examples, the first point is the beginning of a feature in the electronic ECG and the second point is the end of the feature in the electronic ECG. Examples of the feature include a PR interval, a PQ segment, a QRS complex, a QT interval, an ST segment, or an RR interval. According to some cases, the first electronic tip includes a first flag and the second electronic tip includes a second flag. The first electronic tip and the second electronic tip are separated by an interval, which corresponds to the duration of the feature in some examples.

At 1406, the entity outputs duplicated electronic calipers on the electronic ECG. The duplicated electronic calipers are displayed within the GUI along with the electronic ECG and the original electronic caliper. For example, the duplicated electronic calipers are overlaid on and/or intersecting the electronic ECG. The duplicated electronic calipers each include a pair of electronic tips that are separated by the same interval as the first electronic tip and the second electronic tip. According to some implementations, the second electronic tip of the original electronic caliper overlaps with the electronic tip of a duplicated electronic caliper and/or the first electronic tip of the original electronic caliper overlaps with an electronic tip of a duplicated electronic caliper. Thus, in various examples, the duplicated electronic calipers are aligned with the original electronic caliper. In various examples, the display of the duplicated calipers is equivalent to marching the original electronic caliper along the electronic ECG.

Figure 15:
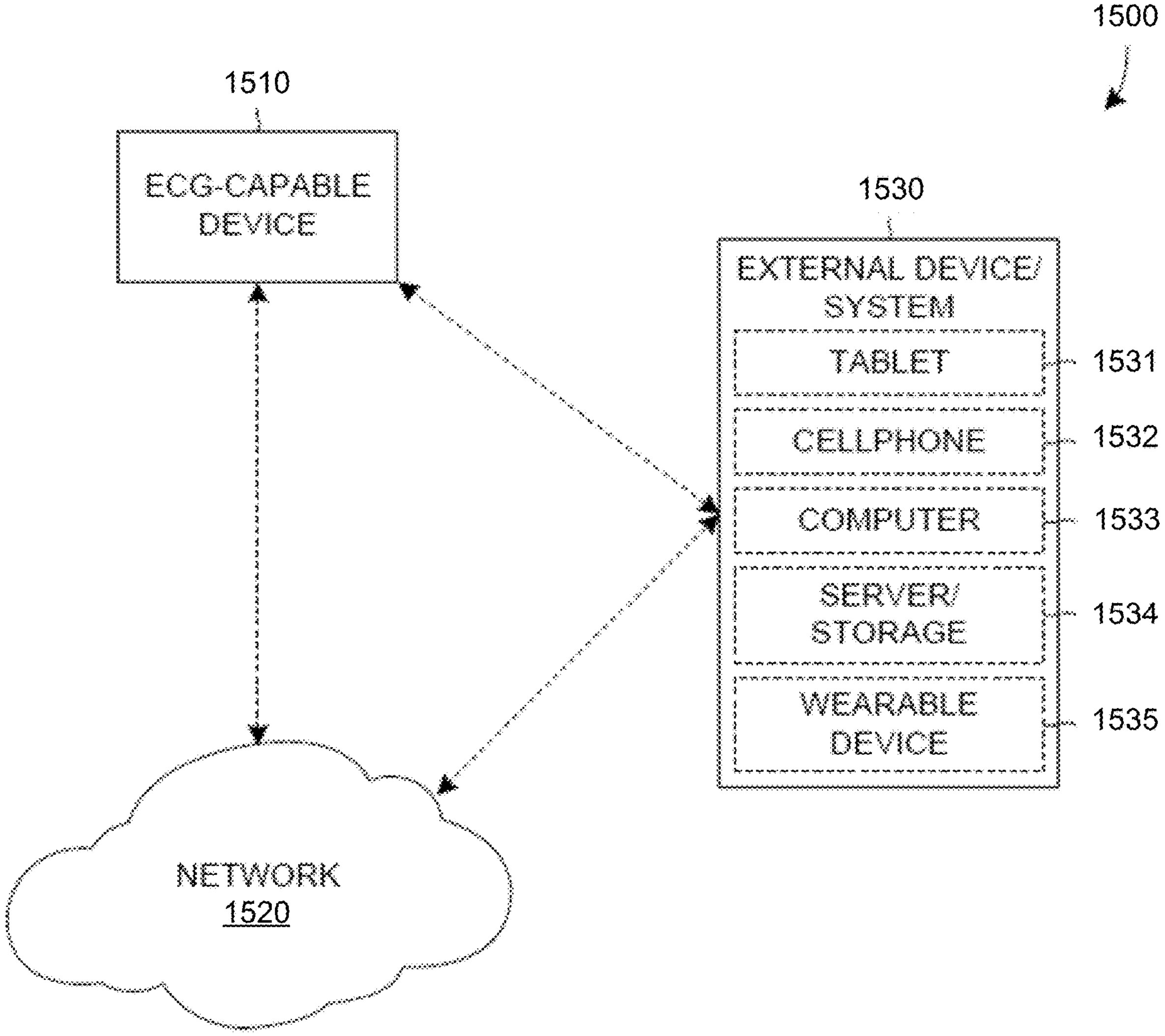
FIG. 15 is an example of communication between an ECG capable device and external device or system.

FIG. 15 illustrates example communications 1500 between an ECG-capable device 1510 and an external device or system 1530, either directly or through a network 1520. The ECG-capable device 1510 is capable of acquiring an ECG signal from a patient. Example ECG-capable devices 1510 can include electrocardiographs, patient monitors, defibrillators, AEDs, monitor-defibrillators, wearable activity monitoring devices, and other devices configured to acquire an ECG signal of a patient. Depending on the ECG-capable device 1510, or the number of leads or sensors coupled thereto, the ECG signal of the patient is a simple ECG signal, such as a one-lead ECG of an AED, or a more complex ECG signal, such as a 12-lead ECG of an electrocardiogram monitor-defibrillator. To assist with analyzing the ECG signal, the ECG-capable device 1510 includes or has an electronic caliper functionality, such as various functionalities described above for outputting and/or manipulating an electronic caliper with the ECG signal. In some examples, the ECG-capable device 1510 provides the ECG signal to an external device or system 1530 that outputs an electronic caliper with the received ECG signal.

In some examples, the ECG signal of the ECG-capable device 1510 is transmitted directly to the external device or system 1530, such as by a direct wired, or wireless, data connection. In some examples, the communication between the ECG-capable device 1510 and the external device or system 1530 is through one or more networks 1520, such as a cellular network, Wi-Fi, Internet, or other network connection accessible to the ECG-capable device 1510. In some cases, the ECG signal is provided in substantially real-time to the external device or system 1530 by the ECG-capable device 1510, or one or more datasets or snapshots of the ECG signal are provided. In some examples, the communication between the ECG-capable device 1510 and one or more external devices or systems 1530 are bi-directional to allow an external device or system 1530 to provide data or other information, such as patient treatment instructions or ECG analysis, to the ECG-capable device 1510.

The external device or system 1530 includes various features and functionality to receive, process, store or analyze an ECG signal, or portion thereof, received from the ECG capable device 1510. For example, the external device or system 1530 includes the electronic caliper functionality described above to assist with analysis of the ECG signal. Additionally, in some examples, the external device or system 1530 provides the ECG analysis, treatment instructions and/or other communications to the ECG-capable device 1510. For example, a remote user uses the external device or system 1530 to receive an ECG signal from the ECG-capable device 1510. The user views and assesses the received ECG signal, such as analyzing the ECG signal using the electronic caliper. Based on the analysis, the user provides treatment instructions to another user of the ECG-capable device 1510, provide additional information regarding a status of the patient based on the received ECG signal, or a combination thereof, in some implementations.

In various cases, the external device or system 1530 provides automated analysis of the ECG signal, or portion(s) thereof, received from the ECG-capable device 1510. In an embodiment, the ECG-capable device 1510 lacks features and functionality of analyzing the received, or acquired, ECG signal of the patient and provides the ECG signal information to the external device or system 1530 for analysis. For example, the ECG-capable device 1510 is an older model or version of a medical device, such as an AED, that lacks hardware or software to analyze a captured ECG signal. In some cases, the medical device is unable to analyze the captured ECG signal as accurately or efficiently as the external device or system 1530. The external device or system 1530 analyzes the captured ECG, automatically or with assistance from a user of the external device or system 1530 and provides analysis or instructions back to the ECG-capable device 1510 to assist with treatment of the patient. In some examples, the external device or system 1530 receives the ECG signal, or portions thereof, for storage to assist with post-event analysis and review or other post-event operations.

Examples of the external devices or system 1530 include a tablet 1531, cellphone 1532, a computer 1533, a server and/or storage device 1534, a wearable device 1535, or other external devices or systems capable of receiving, visualizing, analyzing or receiving user input regarding the ECG signal. The wearable device 1535, for example, includes a smart watch, or smart glasses. Any of the tablet 1531, the cellphone 1532, the computer 1533, the server and/or storage device 1534, or the wearable device 1535, includes an input device (e.g., a touch interface or other interface) to allow one or more users to interact with the received ECG signal, or portion(s) thereof. In various cases, any of the tablet 1531, the cellphone 1532, the computer 1533, the server and/or storage device 1534, or the wearable device 1535 displays the ECG signal to the user and, optionally, displays the electronic caliper to assist with analysis or review of the ECG signal. For example, any of the tablet 1531, the cellphone 1532, the computer 1533, the server and/or storage device 1534, or the wearable device 1535 visually outputs the ECG signal and the electronic caliper via an app, software, hardware, or a combination thereof. Any of the tablet 1531, the cellphone 1532, the computer 1533, the server and/or storage device 1534, or the wearable device 1535 is configured to analyze the ECG signal and/or generate instructions for treating the patient based on the ECG signal. Any of the tablet 1531, the cellphone 1532, the computer 1533, the server and/or storage device 1534, or the wearable device 1535 are configured to transmit communications indicating the analysis and/or instructions to the ECG capable device 1510 over one or more (wired and/or wireless) communication links. In some cases, the ECG capable device 1510, the tablet 1531, the cellphone 1532, the computer 1533, the server and/or storage device 1534, the wearable device 1535, or a combination thereof, is configured to output the analysis and/or instructions regarding the treatment of the patient to a user.

Figure 16:
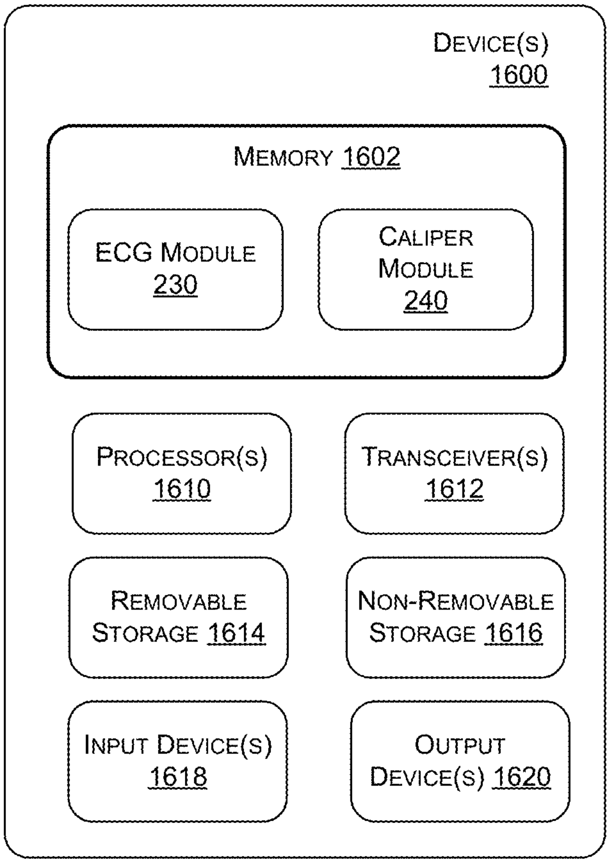
FIG. 16 illustrates an example computing system including at least one device.

FIG. 16 illustrates an example computing system 1600 including at least one device. In some implementations, the system 1600 illustrated in FIG. 16 is configured to perform any of the functionality described herein. The system 1600 is implemented by at least one of server computer(s), dedicated hardware, software operating on dedicated hardware, or virtualized function(s) hosted on an appropriate platform (e.g., as cloud infrastructure). In some cases, the system 1600 is implemented as a single device or as multiple devices with components and data distributed among them.

As illustrated, the system 1600 includes a memory 1602. In various implementations, the memory 702 is volatile (such as random access memory (RAM)), non-volatile (such as read only memory (ROM), flash memory, etc.) or some combination of the two. Various elements stored in the memory 1602 include methods, threads, processes, applications, objects, modules, any other sort of executable instructions, or a combination thereof. Elements stored in the memory 1602 may be non-transitory. The memory 1602 stores various files, databases, or the like, in some cases.

The memory 1602 includes various instructions 1604, which are for executing any of the functionality described herein. For example, the memory 1602 stores the ECG module 230 and the caliper module 240 described above with reference to FIG. 2. The ECG module 230 and the caliper module 240 include instructions for performing various functions, such as displaying (e.g., activating) an electronic ECG, displaying an electronic caliper, scrolling the electronic ECG, marching the electronic caliper, repositioning one or more tips of the electronic caliper, identifying a selected feature in the electronic ECG, identifying a duration of a feature in the electronic ECG, identifying a time period corresponding to an interval between the tips of the electronic caliper, displaying a grid, or any combination thereof.

In various examples, the instructions 1604, the ECG module 230, and the caliper module 240 are executed by processor(s) 1610 to perform operations. In some embodiments, the processor(s) 1610 includes a central processing unit (CPU), a graphics processing unit (GPU), or both CPU and GPU, or other processing unit or component known in the art.

As illustrated in FIG. 16, the system 1600 also includes one or more wired or wireless transceiver(s) 1612. For example, the transceiver(s) 1612 include, for example, a network interface card (NIC), a network adapter, a local area network (LAN) adapter, or a physical, virtual, or logical address to connect to the various external devices and/or systems. In various examples, the transceiver(s) 1612 include any sort of wireless transceivers capable of engaging in wireless communication (e.g., radio frequency (RF) communication). In some cases, the transceiver(s) 1612 include other wireless modems, such as a modem for engaging in WI-FI®, WIGIG®, WIMAX®, BLUETOOTH®, or infrared communication. For example, the system 1600 is configured to transmit and/or receive data (e.g., ECG data) with one or more external devices.

In some examples, the system 1600 also includes additional data storage components such as, for example, magnetic disks, optical disks, or tape. These additional data storage components include removable storage 1614 and non-removable storage 1616. Tangible computer-readable media include volatile and nonvolatile, removable and non-removable media implemented in any method or technology for storage of information, such as computer readable instructions, data structures, program modules, or other data.

The memory 1602, removable storage 1614, and non-removable storage 1616 are all examples of computer-readable storage media. Computer-readable storage media include, but are not limited to, RAM, ROM, EEPROM, flash memory or other memory technology, CD-ROM, Digital Versatile Discs (DVDs), Content-Addressable Memory (CAM), or other optical storage, magnetic cassettes, magnetic tape, magnetic disk storage or other magnetic storage devices, or any other medium which can be used to store the desired information and which can be accessed by the system 1600. Any such tangible computer-readable media can be part of the system 1600. In various examples, any portion of ECG data, numerical values indicative of intervals in the ECG data and/or separating tips of an electronic caliper, are stored in the memory 1602, removeable storage 1614, non-removable storage 1616, or a combination thereof.

In various cases, the system 1600 also includes input device(s) 1618 and output device(s) 1620. In some implementations, the input device(s) 1620 includes at least one of a keypad, a cursor control, a touch-sensitive display, a voice input device, a haptic feedback device, or any combination thereof. According to some implementations, the input device(s) 1620 are configured to receive one or more user input signals. In some cases, the input device(s) 1618 include one or more physiological parameter sensors, such as electrodes and/or a detection circuit configured to generate an ECG signal based on a difference between voltages of the electrodes. The output device(s) 722 can include at least one of a display, speakers, a haptic output device, printers, etc. In some implementations, the input device(s) 1618 include one or more touch sensors, the output device(s) 1620 include a display screen, and the touch sensor(s) are integrated with the display screen. Thus, in some cases, the system 1600 includes a touchscreen configured to receive user input signal(s) and visually output an ECG as well as the electronic caliper.

Example Clauses

1. A monitor-defibrillator, including: an electrocardiogram (ECG) port configured to receive an ECG signal; a display configured to display the ECG signal; a processor configured to: cause caliper to activate, the activated caliper displaying a first bound and a second bound overlaid on the displayed ECG signal on the display; receive a first user selection to position the first bound of the caliper over a first selection on the ECG signal; receive a second user selection to position the second bound of the caliper over a second selection on the ECG signal; define a caliper interval between the first bound and the second bound; and receive user input to move one or both of the displayed ECG signal relative to the caliper interval and the caliper interval relative to the displayed ECG signal; wherein the display is further configured to display received user input to move the one or both of the displayed ECG signal and the caliper interval.
2. The monitor-defibrillator of clause 1, wherein the ECG port is coupled to one or more sensors configured to sense one or more physiological parameters of a patient, at least one of the physiological parameters being representative of an ECG signal of the patient.
3. The monitor-defibrillator of clause 1 or 2, wherein the display is a touchscreen and wherein the first and second user selections are received based on a user interaction with the touchscreen.
4. The monitor defibrillator of clause 3, wherein the touchscreen is configured to receive the user input to move the displayed ECG signal relative to the caliper interval and wherein the movement of the displayed ECG signal is based on the received user input.
5. The monitor defibrillator of clause 3 or 4, wherein the touchscreen is configured to receive the user input and move the caliper interval relative to the displayed ECG signal and wherein the movement of the caliper interval is based on the received user input.

6. The monitor-defibrillator of any one of clauses 1 to 5, wherein the processor is further configured to calculate a duration of the interval and wherein the display is further configured to display the calculated duration of the interval.
7. The monitor-defibrillator of any one of clauses 1 to 6, wherein the processor is configured to duplicate the interval and cause the display to display the duplicated intervals along the ECG signal.
8. The monitor-defibrillator of any one of clauses 1 to 7, wherein the processor is further configured to receive a user input to view at least one of a preceding portion or a proceeding portion of the ECG signal and wherein the display is configured to display at least a portion of the displayed ECG signal and the at least one of a preceding portion or a proceeding portion of the ECG signal.
9. The monitor-defibrillator of any one of clauses 1 to 8, wherein the processor is further configured to receive a user input to display a grid on the displayed ECG signal, the processor aligning the grid with at least the first bound of the caliper and wherein the display is further configured to display the grid on the displayed ECG signal.
10. A monitor-defibrillator, including: an electrocardiogram (ECG) port configured to receive an ECG signal; a display configured to display the ECG signal; a processor configured to: cause caliper to activate, the activated caliper displaying a first bound and a second bound overlaid on the displayed ECG signal on the display; receive a first user selection to position the first bound of the caliper over a first selection on the displayed ECG signal; receive a second user selection to position the second bound of the caliper over a second selection on the displayed ECG signal; define a caliper interval between the first bound and the second bound; and receive user input to move the caliper interval from a first position on the displayed ECG signal to a second position on the displayed ECG signal, wherein the display is further configured to display received user input to move the caliper interval from the first position to the second position on the displayed ECG signal.
11. The monitor-defibrillator of clause 10, wherein the processor is further configured to receive a user input to duplicate the interval across the displayed ECG signal, with at least a second bound of a first instance of the duplicated interval substantially aligned with the first bound of a second instance of the duplicated interval, and wherein the display is further configured to display the duplicated interval on the displayed ECG signal.
12. The monitor-defibrillator of clause 11, wherein the processor is further configured to receive a user input to view at least one of a preceding portion or a proceeding portion of the ECG signal and to duplicate the interval across the at least a portion of the displayed ECG signal and the at least one of a preceding portion or a proceeding portion of the ECG signal, and wherein the display is configured to display the at least a portion of the displayed ECG signal and the at least one of a preceding portion or a proceeding portion of the ECG signal with the duplicated interval.
13. The monitor-defibrillator of any one of clauses 10 to 12, wherein the processor is further configured to analyze the ECG signal to identify one or more features of the ECG signal and to receive a user input selecting a feature of the one or more feature of the ECG signal, the first user selection and the second user selection being determined from the selected feature with the first user selection being a beginning of the selected feature and the second user selection being an ending of the selected feature, and wherein the first bound of the caliper is automatically positioned at the beginning of the selected feature based on the analysis of the ECG signal and wherein the second bound of the caliper is automatically positioned at an end of the selected feature based on the analysis of the ECG signal.
14. The monitor-defibrillator of any one of clauses 10 to 13, wherein the processor is further configured to determine at least one of a length or duration of the interval and wherein the display is further configured to display the at least one of a length or duration of the interval.
15. A monitor-defibrillator, including: an electrocardiogram (ECG) port configured to receive an ECG signal; a display configured to display the ECG signal; a processor configured to: cause caliper to activate, the activated caliper displaying a first bound and a second bound overlaid on the displayed ECG signal on the display; receive a first user selection to position the first bound of the caliper over a first selection on the ECG signal; receive a second user selection to position the second bound of the caliper over a second selection on the ECG signal; define a caliper interval between the first bound and the second bound; and receive user input to move the ECG signal with respect to the caliper interval, wherein the display is further configured to display received user input to move the ECG signal with respect to the caliper interval.
16. The monitor-defibrillator of clause 15, wherein the display includes a touch interface through which the first and second user selections are received.
17. The monitor-defibrillator of clause 15 or 16, wherein the user input to move the ECG signal with respect to the caliper interval is received through an interaction with the displayed ECG signal on the display.
18. The monitor-defibrillator of any one of clauses 15 to 17, wherein an amount of the movement of the ECG signal with respect to the caliper interval is based on the user input.
19. A monitor-defibrillator, including: an output with a display configured to display an ECG signal; a processor configured to: cause caliper to activate, the activated caliper displaying a first bound and a second bound overlaid on the displayed ECG signal on the display; define a caliper interval between the first bound and the second bound; and receive user input to move one or both of the displayed ECG signal and the caliper interval with respect to each other; wherein the display is further configured to display the movement of the one or both of the displayed ECG signal and the caliper interval.
20. The monitor-defibrillator of clause 19, wherein the ECG signal is captured by the monitor-defibrillator.
21. The monitor-defibrillator of clause 19 or 20, wherein the display is a touchscreen.
22. The monitor-defibrillator of clause 21, wherein user input to move one or both of the displayed ECG signal and the caliper interval with respect to each other is received through the touchscreen.
23. The monitor-defibrillator of clause 22, wherein an amount of the movement of the one or both of the displayed ECG signal and the caliper interval is based on the user input.

24. The monitor-defibrillator of any one of clauses 19 to 23, wherein the processor is further configured to analyze the ECG signal for one or more features and receive a user input selecting a feature of the one or more features of the ECG signal and wherein the first bound is overlaid on the displayed ECG signal at a beginning of the selected feature and the second bound is overlaid on the displayed ECG signal at an end of the selected feature.
25. The monitor-defibrillator of clause 24, wherein the feature is selected from a list of the one or more features.
26. The monitor-defibrillator of any one of clauses 19 to 25, wherein the processor is further configured to repeat the interval along the ECG signal and wherein the display is further configured to display the repeated intervals on the displayed ECG signal.
27. The monitor-defibrillator of any one of clauses 19 to 26, wherein the processor is further configured to receive a user input to display a grid on the displayed ECG signal and wherein the display is further configured to display the grid on the displayed ECG signal, the grid being aligned with at least one of the first or the second bound of the caliper.
28. The monitor-defibrillator of clause 27, wherein a scale of the grid is variable and wherein the processor is configured to receive one of a user input of the scale of the grid or to select the scale of the grid based on at least a length or duration of the displayed ECG signal.
29. The monitor-defibrillator of any one of clauses 19 to 28, wherein the processor is further configured to receive a user input of at least a length or a duration of the caliper interval, the first and second bounds displayed having the caliper interval therebetween.
30. The monitor-defibrillator of clause 29, wherein the user input of at least a length or a duration of the caliper interval is a selection of one of a plurality of predetermined lengths or durations of the caliper interval.
31. An medical external device, including: a processor configured to: receive an electrocardiogram (ECG) signal from an ECG-capable device; cause the received ECG signal to be displayed on a display; cause caliper to activate, the activated caliper displaying a first bound and a second bound overlaid on the displayed ECG signal on the display; receive a first user selection to position the first bound of the caliper over a first selection on the ECG signal; receive a second user selection to position the second bound of the caliper over a second selection on the ECG signal; define a caliper interval between the first bound and the second bound; receive user input to move one or both of the displayed ECG signal relative to the caliper interval and the caliper interval relative to the displayed ECG signal; and cause the one or both of the displayed ECG signal and the caliper interval to be moved in response to the received user input.
32. The external device of clause 31, further including the display, the display configured to display the ECG signal and wherein the display is a touchscreen and the first and second user selections are received based on a user interaction with the touchscreen.
33. The external device of clause 32, wherein the touchscreen is configured to receive the user input to move the displayed ECG signal relative to the caliper interval and wherein the movement of the displayed ECG signal is based on the received user input.
34. The external device of clause 32 or 33, wherein the touchscreen is configured to receive the user input and move the caliper interval relative to the displayed ECG signal and wherein the movement of the caliper interval is based on the received user input.
35. The external device of any one of clauses 31 to 34, wherein the processor is further configured to calculate a duration of the interval and to cause the calculated duration of the interval to be displayed.
36. The external device of any one of clauses 31 to 35, wherein the processor is configured to duplicate the interval and cause the duplicated intervals to be displayed along the ECG signal.
37. The external device of any one of clauses 31 to 36, wherein the processor is further configured to receive a user input to view at least one of a preceding portion or a proceeding portion of the ECG signal and to cause the at least a portion of the displayed ECG signal and the at least one of a preceding portion or a proceeding portion of the ECG signal to be displayed.
38. The external device of any one of clauses 31 to 37, wherein the processor is further configured to receive a user input to display a grid on the displayed ECG signal and to cause the grid to be displayed on the displayed ECG signal, the processor aligning the grid with at least the first bound of the caliper.
39. The external device of any one of clauses 31 to 38, wherein the ECG signal from an ECG-capable device is communicated through a network to the external device.
40. The external device of any one of clauses 31 to 39, wherein the processor is further configured to cause the received ECG signal to be stored.
41. A defibrillator, comprising: a detection circuit configured detect a voltage output by the heart of a patient; a touchscreen configured to display a graphical user interface (GUI) and to receive a first input and a second input from a user; a processor; and memory storing instructions that, when executed by the processor, cause the processor to perform operations comprising: causing the touchscreen to display, based on the voltage output by the heart of the patient, an electronic electrocardiogram (ECG) within the GUI; determining that the first input selects a first instance of a feature of the electronic ECG, the feature being defined between a first point of the electronic ECG and a second point of the electronic ECG; causing the touchscreen to display, at a first position within the GUI, an electronic caliper that comprises a first electronic tip overlaid on the first point and a second electronic tip overlaid on the second point, an interval between the first electronic tip and the second electronic tip defining a duration; determining that the second input selects a second instance of the feature defined between a third point of the electronic ECG and a fourth point of the electronic ECG; and causing the touchscreen to display, at a second position within the GUI, the electronic caliper by overlaying the first electronic tip on the third point of the electronic ECG.
42. The defibrillator of clause 41, wherein the operations further comprise: causing the touchscreen to output an indication of the duration.
43. The defibrillator of clause 41 or 42, wherein causing the touchscreen to display, at the second position within the GUI, the electronic caliper comprises maintaining the interval between the first electronic tip and the second electronic tip.

44. A method for patient monitoring, the method comprising: outputting, by a display, an electronic electrocardiogram (ECG) within a graphical user interface (GUI); outputting, by the display, an electronic caliper overlaid on the electronic ECG within the GUI, the electronic caliper comprising a first electronic tip and a second electronic tip; receiving, by a user input device, a user input signal; and moving, based on the user input signal, the first electronic tip, the second electronic tip, or both the first electronic tip and the second electronic tip, relative to the electronic ECG within the GUI.

45. The method of clause 44, further comprising: outputting a grid within the GUI, a gridline of the grid overlapping the first electronic tip.

46. The method of clause 44 or 45, the user input signal being a first user input signal, wherein outputting the electronic caliper overlaid on the electronic ECG within the GUI comprises: receiving, by the input device, a second user input signal; identifying, based on the second user input signal, a feature of the electronic ECG; outputting the first electronic tip overlaid on a first point of the electronic ECG that corresponds to the beginning of the feature; and causing the display to output the second electronic tip overlaid on a second point of the electronic ECG that corresponds to the end of the feature.

47. The method of clause 46, wherein the feature comprises a PR interval, a PQ segment, a QRS complex, a QT interval, an ST segment, or an RR interval.

48. The method of clause 46 or 47, wherein the first electronic tip overlaid on the first point and the second electronic tip overlaid on the second point are separated by an interval, wherein the first point corresponds to the beginning of a first instance of the feature and the second point corresponds to the end of the first instance of the feature, and wherein moving the first electronic tip and the second electronic tip comprises: outputting, by the display, the first electronic tip overlaying a third point of the electronic ECG, the third point corresponding to the beginning of a second instance of the feature; and outputting, by the display, the second electronic tip separated from the first electronic tip by the interval.

49. The method of any one of clauses 44 to 48, wherein the first electronic tip and the second electronic tip are separated by an interval, the method further comprising: outputting, by the display, a duplicated electronic caliper overlaid on the electronic ECG within the GUI, the duplicated electronic caliper comprising a third electronic tip and a fourth electronic tip that are separated by the interval.

50. The method of any one of clauses 44 to 49, wherein the first electronic tip and the second electronic tip are separated by an interval, the method further comprising: outputting, by the display within the GUI, a numerical value indicating a time period that corresponds to the interval.

51. The method of any one of clauses 44 to 50, the user input signal being a first user input signal, the method further comprising: receiving, by the input device, a second user input signal; and scrolling, based on the second user input signal, the electronic ECG within the GUI.

52. The method of any one of clauses 44 to 51, the user input signal being a first user input signal, the method further comprising: receiving, by the input device, a second user input signal; and zooming in or zooming out, based on the second user input signal, the electronic ECG within the GUI.

53. A system comprising a processor; and memory storing instructions that, when executed by the processor, cause the system to perform operations comprising the method of any one of clauses 44 to 52.

54. The system of clause 53, further comprising a display configured to output the GUI.

55. The system of clause 53 or 54, further comprising an input device configured to receive one or more user input signals.

56. The system of any one of clauses 53 to 55 further comprising a detection circuit configured to receive a voltage and to generate the electronic ECG based on the voltage.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing the invention in diverse forms thereof.

As will be understood by one of ordinary skill in the art, each implementation disclosed herein can comprise, consist essentially of or consist of its particular stated element, step, or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the implementation to the specified elements, steps, ingredients or components and to those that do not materially affect the implementation. As used herein, the term "based on" is equivalent to "based at least partly on," unless otherwise specified.

The invention claimed is:

1. A monitor, comprising:

a first sensor configured to detect a physiological parameter of a patient;

a display configured to present a graphical representation of the physiological parameter and to present repeated calipers overlaid on the graphical representation of the physiological parameter;

a second sensor configured to detect an input signal from a user, the input signal corresponding to a movement of a tip of a caliper among the repeated calipers; and a processor configured to:

in response to the input signal:

cause the display to move the tip of the caliper; and cause the display to move the repeated calipers from first positions to second positions, an interval between the repeated calipers at the first positions being different than an interval between the repeated calipers at the second positions.

2. The monitor of claim 1, wherein the physiological parameter comprises an electrical impedance, a heart rate, a blood oxygenation, a partial pressure of CO2, a blood pressure, or a pulse rate.

3. The monitor of claim 1, the tip being a first tip, wherein the repeated calipers further comprise a second tip, a third tip, and a fourth tip, wherein the interval between the repeated calipers at the first positions corresponds to a first distance between the first tip and the second tip and the first distance between the third tip and the fourth tip, and wherein the interval between the repeated calipers at the second positions corresponds to a second distance between the first tip and the second tip and the second distance between the third tip and the fourth tip.

4. A medical device, comprising:

a display configured to present a graphical representation of a physiological parameter of a patient and to present repeated calipers comprising a caliper overlaid on the graphical representation of the physiological parameter;

a sensor configured to detect an input signal from a user, the input signal corresponding to a movement of a tip of the caliper; and a processor configured to:

in response to the input signal, cause the display to move the tip of the caliper by:

moving the repeated calipers from first positions to second positions, an interval between the repeated calipers at the first positions being different than an interval between the repeated calipers at the second positions, the tip of the caliper being moved from one of the first positions to one of the second positions.

5. The medical device of claim 4, wherein the physiological parameter comprises an electrical impedance, a heart rate, a blood oxygenation, a partial pressure of CO2, a blood pressure, or a pulse rate.

6. The medical device of claim 4, wherein the sensor is integrated with the display, and wherein the input signal comprises a touch of the user.

7. The medical device of claim 4, wherein the tip is a first tip of the caliper, and wherein the processor is configured to cause the display to move the first tip of the caliper by changing a distance between the first tip of the caliper and a second tip of the caliper.

8. The medical device of claim 7, wherein the graphical representation of the physiological parameter of the patient comprises a waveform of the physiological parameter with respect to time, and wherein the processor is further configured to:

in response to causing the display to move the first tip of the caliper, causing the display to output an indication of a time period corresponding to the distance between the first tip of the caliper and the second tip of the caliper.

9. The medical device of claim 4, the tip being a first tip of the caliper, wherein the processor is further configured to cause the display to move the first tip of the caliper by:

moving the first tip of the caliper and a second tip of the caliper from first positions to second positions, a distance between the first positions being equivalent to a distance between the second positions.

10. The medical device of claim 4, wherein the processor is further configured to:

in response to the tip being moved within a predetermined distance of an edge of the display, cause the display to scroll the graphical representation of the physiological parameter from a first segment of the physiological parameter to a second segment of the physiological parameter.

11. A method, comprising:

presenting, by a display, a graphical representation of a physiological parameter of a patient;

presenting, by the display, a caliper overlaid on the graphical representation of the physiological parameter by presenting, by the display, repeated calipers overlaid on the graphical representation of the physiological parameter, the repeated calipers comprising the caliper;

detecting, from a user, an input signal corresponding to a movement of a tip of the caliper; and in response to detecting the input signal, moving, by the display, the tip of the caliper with respect to the graphical representation of the physiological parameter by moving the repeated calipers from first positions to second positions, an interval between the repeated calipers at the first positions being different than an interval between the repeated calipers at the second positions, the tip of the caliper being moved from one of the first positions to one of the second positions.

12. The method of claim 11, wherein the physiological parameter comprises an electrical impedance, a heart rate, a blood oxygenation, a partial pressure of CO2, a blood pressure, or a pulse rate.

13. The method of claim 11, wherein detecting, from the user, the input signal corresponding to the movement of the tip of the caliper comprises detecting a touch of the user.

14. The method of claim 11, the tip being a first tip of the caliper, wherein moving, by the display, the tip of the caliper with respect to the graphical representation of the physiological parameter comprises:

changing, by the display, a distance between the first tip of the caliper and a second tip of the caliper.

15. The method of claim 11, the tip being a first tip of the caliper, wherein the graphical representation of the physiological parameter of the patient comprises a waveform of the physiological parameter with respect to time, and wherein the method further comprises:

in response to causing the display to move the first tip of the caliper, causing the display to output an indication of a time period corresponding to a distance between the first tip of the caliper and a second tip of the caliper.

16. The method of claim 11, the tip being a first tip of the caliper, the method further comprising: moving, by the display, the first tip of the caliper by:

moving the first tip of the caliper and a second tip of the caliper from first positions to second positions, a distance between the first positions being equivalent to a distance between the second positions.

17. The method of claim 11, further comprising in response to the tip being moved within a predetermined distance of an edge of the display, scrolling, by the display, the graphical representation of the physiological parameter from a first segment of the physiological parameter to a second segment of the physiological parameter.

* * * * *